US012738358B2

(12) United States Patent
Areias et al.

(10) Patent No.: US 12,738,358 B2
(45) Date of Patent: Sep. 15, 2026

(54) ARTIFICIAL INTELLIGENCE-DRIVEN PREDICTIVE TOOL FOR DIGITAL PLATFORMS

(71) Applicant: Sword Health, S.A., Oporto (PT)

(72) Inventors: Anabela Cepa Areias, Oporto (PT); Robert Moulder, Draper, UT (US); Fabíola Costa, Oporto (PT); Maria Molinos, Oporto (PT); Dora Janela, Oporto (PT); Fernando Correia, Oporto (PT); Virgílio António Ferro Bento, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 138 days.

(21) Appl. No.: 18/395,359

(22) Filed: Dec. 22, 2023

(65) Prior Publication Data

US 2025/0210176 A1 Jun. 26, 2025

(51) Int. Cl.

| | |
|---|---|
| ***G16H 20/30*** | (2018.01) |
| ***G16H 10/20*** | (2018.01) |
| ***G16H 10/60*** | (2018.01) |
| ***G16H 15/00*** | (2018.01) |

(52) U.S. Cl.

CPC ............ *G16H 20/30* (2018.01); *G16H 10/20* (2018.01); *G16H 10/60* (2018.01); *G16H 15/00* (2018.01)

(58) Field of Classification Search

None

See application file for complete search history.

(56) References Cited

U.S. PATENT DOCUMENTS

| | | | |
|---|---|---|---|
| 11,537,888 | B2 | 12/2022 | Banisakher et al. |
| 11,704,582 | B1 | 7/2023 | Jain et al. |
| 2011/0119212 | A1 | 5/2011 | De Bruin et al. |

(Continued)

FOREIGN PATENT DOCUMENTS

| | | | |
|---|---|---|---|
| WO | WVO-2017106770 | A1 | 6/2017 |
| WO | WO-2022256018 | A1 | 12/2022 |

OTHER PUBLICATIONS

Aasdahl, Lene, et al., "Recovery trajectories in common musculo-skeletal complaints by diagnosis contra prognostic phenotypes", BMC Musculoskelet Disord, 22, 455, (2021), 1-11.

(Continued)

*Primary Examiner* — John A Pauls

(74) *Attorney, Agent, or Firm* — SCHWEGMAN LUNDBERG & WOESSNER, P.A.

(57) ABSTRACT

Examples described herein relate to an artificial intelligence-driven tool for digital physical therapy. First data indicative of a baseline condition of a first user is accessed. Second data is collected for each of a plurality of sessions of a digital physical therapy program. A first device associated with the first user tracks motion of the first user during each session. Input data based on the first data and the second data is provided to a machine learning classifier to cause generation of output data indicative of a predicted outcome of the digital physical therapy program. The predicted outcome is processed to detect that the first user is predicted not to meet a predetermined improvement threshold. An alert is generated and presented at a second device associated with a second user administering the digital physical therapy program.

20 Claims, 7 Drawing Sheets

(56) References Cited

U.S. PATENT DOCUMENTS

| | | | | |
|---|---|---|---|---|
| 2013/0178960 | A1* | 7/2013 | Sheehan | G16H 40/67 700/91 |
| 2019/0066832 | A1* | 2/2019 | Kang | A61B 5/1128 |
| 2019/0091511 | A1* | 3/2019 | Christoforou | A63B 21/00189 |
| 2020/0168335 | A1* | 5/2020 | Lassoued | G16H 40/67 |
| 2020/0246658 | A1* | 8/2020 | Small | A63B 21/4033 |
| 2020/0410339 | A1 | 12/2020 | Otsuki et al. | |
| 2022/0223255 | A1 | 7/2022 | Kraal et al. | |
| 2022/0328198 | A1 | 10/2022 | Wasan et al. | |
| 2022/0375568 | A1 | 11/2022 | Hosoi et al. | |
| 2024/0260892 | A1* | 8/2024 | Haas | A61B 5/4824 |

OTHER PUBLICATIONS

Boersma, Katja, et al., "Early Identification of Patients at Risk of Developing a Persistent Back Problem: The Predictive Validity of the Örebro Musculoskeletal Pain Questionnaire", Clin J Pain, 19, (2003), 80-86.

Brennan, Gerard, et al., "Significant Clinical Improvement Was Predicted in a Cohort of Patients with Low Back Pain Early in the Care Process", Physical Therapy, 103, (2023), 1-10.

Cecchi, F, et al., "Predictors of response to exercise therapy for chronic low back pain: result of a prospective study with one year follow-up", Eur J Phys Rehabil Med, 50(2), (2014), 143-151.

Cholewicki, Jacek, et al., "Can Biomechanics Research Lead to More Effective Treatment of Low Back Pain? A Point-Counterpoint Debate", Journal of Orthopaedic & Sports Physical Therapy. vol. 49, No. 6, (Jun. 2019), 425-436.

Cholewicki, Jacek, et al., "Development of a collaborative model of low back pain: report from the 2017 NASS consensus meeting (accepted manuscript)", The Spine Journal, (2018), 38 pgs.

Cook, Chad, et al., "Which Prognostic Factors for Low Back Pain Are Generic Predictors of Outcome Across a Range of Recovery Domains?", Physical Therapy vol. 93 No. 1, (Jan. 2013), 32-40.

Cruz, Eduardo, et al., "Prognostic indicators for poor outcomes in low back pain patients consulted in primary care", Plos One 15, e0229265, (Mar. 27, 2020), 1-15.

Cui, D, et al., "Randomized-controlled trial assessing a digital care program versus conventional physiotherapy for chronic low back pain", npj Digital Medicine 6, 121, (2023), 10 pgs.

Hay, Elaine, et al., "A randomised clinical trial of subgrouping and targeted treatment for low back pain compared with best current care. The STarT Back Trial Study Protocol", BMC Musculoskelet Disord 9, 58, (2008), 1-9.

Hill, Jonathan, et al., "A Primary Care Back Pain Screening Tool: Identifying Patient Subgroups for Initial Treatment", Arthritis Rheum, 59(5), (2008), 632-641.

Hockings, Rowena, et al., "A Systematic Review of the Predictive Ability of the Orebro Musculoskeletal Pain Questionnaire", Spine, 33(15), (2008), E494-E500.

Hyland, Stephanie, et al., "Early prediction of circulatory failure in the intensive care unit using machine learning", Nature Medicine, vol. 26, (Mar. 2020), 364-373.

Kendall, Michelle, et al., "The predictive ability of the STarT Back Tool was limited in people with chronic low back pain: a prospective cohort study", Journal of Physiotherapy, 64, (2018), 107-113.

Lentz, Trevor, et al., "Development of a Yellow Flag Assessment Tool for Orthopaedic Physical Therapists: Results from the Optimal Screening for Prediction of Referral and Outcome (OSPRO) Cohort", Journal of Orthopaedic & Sports Physical Therapy, vol. 46, No. 5, (May 2016), 327-345.

Lundberg, Scott, et al., "From local explanations to global understanding with explainable AI for trees", Nat Mach Intell., 2(1), 56-67, (Jan. 2020), 27 pgs.

Mork, P J, et al., "Decision Support System to EnhancePain: Protocol for the selfBACK Project", JMIR Res Protoc.from the Internet: <URL: https://www.researchgate.net/publication/324608516_A_Decision_Support_System_to_Enhance_Self-Management_of_Low_Back_Pain_Protocol_for_the_selfBACK_Project, (2018), 1-12.

Nieminen, Linda, et al., "Prognostic factors for pain chronicity in low back pain: a systematic review", PAIN Reports 6(1): e919, (Apr. 2021), 1-17.

Nijeweme-D'Hollosy Wendy, et al., "Evaluation of three machine learning models for self-referral decision support on low back pain in primary care", International Journal of Medical Informatics, 110, (2018), 31-41.

Nim, Casper G, et al., "Do Visual Pain Trajectories Reflect the Actual Course of Low Back Pain?", The Journal of Pain, vol. 24, No. 8, (Aug. 2023), 1506-1521.

Pak, S, et al., "Comparing Digital to Conventional Physical Therapy for Chronic Shoulder Pain: Randomized Controlled Trial", J Med Internet Res, 25, e49236, (2023), 1-18.

Placido, D., "A deep learning algorithm to predict risk of pancreatic cancer from disease trajectories", Nature Medicine, vol. 29, (May 2023), 1113-1122.

Raiszadeh, Kamshad, et al., "In-Clinic Versus Web-Based Multidisciplinary Exercise-Based Rehabilitation for Treatment of Low Back Pain: Prospective Clinical Trial in an Integrated Practice Unit Model", J Med Internet Res, vol. 23, iss. 3, e22548, (2021), 13 pgs.

Sun, Xu, et al., "Fast Implementation of DeLong's Algorithm for Comparing the Areas Under Correlated Receiver Operating Characteristic Curves", IEEE Signal Processing Letters 21, (2014), 1389-1393.

Tagliaferri, Scott, et al., "Chronic back pain sub-grouped via psychosocial, brain and physical factors using machine learning", Scientifc Reports, 12:15194, (2022), 1-15.

Tagliaferri, Scott, et al., "Classifying Nonspecific Low Back Pain for Better Clinical Outcomes: Current Challenges and Paths Forward", J Orthop Sports Phys Ther, 53(5), (2023), 12 pgs.

Toelle, Thomas, et al., "App-based multidisciplinary back pain treatment versus combined physiotherapy plus online education: a randomized controlled trial", npj Digital Medicine, 34, (2019), 1-9.

Toh, Irene, et al., "Evaluation of the STarT Back Screening Tool for Prediction of Low Back Pain Intensity in an Outpatient Physical Therapy Setting", Journal of Orthopaedic & Sports Physical Therapy, 47(4), (2017), 261-267.

Traeger, Adrian, "Estimating the Risk of Chronic Pain: Development and Validation of a Prognostic Model (PICKUP) for Patients with Acute Low Back Pain", PLOS Medicine, 13(5), (May 17, 2016), 1-21.

Zmudski, Fredrick, et al., "Machine learning clinical decision support for interdisciplinary multimodal chronic musculoskeletal pain treatment", Front Pain Res, 4, 1177070, (May 9, 2023), 1-18.

Qiu, Fanji, et al., "Use of artificial neural networks in the prognosis of musculoskeletal diseases—a scoping review", BMC Musculoskeletal Disorders, 24:86, (2023), 1-11.

Tschuggnall, Michael, et al., "Machine learning approaches to predict rehabilitation success based on clinical and patient-reported outcome measures", Informatics in Medicine Unlocked, 24, 100598, (2021), 1-10.

* cited by examiner

ARTIFICIAL INTELLIGENCE-DRIVEN PREDICTIVE TOOL FOR DIGITAL PLATFORMS

TECHNICAL FIELD

The subject matter of this disclosure relates, generally, to the field of artificial intelligence-driven predictive technology. More specifically, but not exclusively, subject matter herein relates to an automated, predictive tool for use in systems and methods for providing digital physical therapy.

BACKGROUND

A patient suffering from a condition that causes physical pain or discomfort, such as a musculoskeletal (MSK) condition, can be treated by way of physical therapy sessions. Digital physical therapy has emerged as an effective technological solution that facilitates rehabilitation of patients suffering from, for example, MSK conditions (e.g., low back pain (LBP)). As used herein, the term "digital physical therapy" refers to physical therapy services delivered using one or more digital communication modalities and electronic devices.

By leveraging digital physical therapy technology, a patient can consult virtually with a physical therapist and perform exercises at a remote location (e.g., at home) while a digital therapy platform automatically tracks certain progress of the patient. For example, the digital therapy platform can monitor whether and how the exercises are performed via motion trackers, vital sign sensors, computer vision technology, user-reported feedback, or combinations thereof. In this way, digital physical therapy can obviate or reduce the need for constant human monitoring of a patient or in-person visits to a hospital or other therapy facility.

While digital physical therapy technology may assist with patient treatment or rehabilitation, it can be challenging to establish or predict whether a particular patient will respond positively to therapy. For example, while a digital physical therapy platform includes technological components that enable it to track overall program adherence and patient activity during each session of a digital physical therapy program, it may lack the capability to accurately predict, prior to conclusion of a digital physical therapy program, whether the patient will be pain-free or will achieve a significant reduction in pain upon conclusion of the digital physical therapy program. These and other technical limitations may restrict the utility (and thus also wider adoption) of digital physical therapy technology.

BRIEF DESCRIPTION OF THE SEVERAL VIEWS OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some non-limiting examples are illustrated in the figures of the accompanying drawings in which.

DETAILED DESCRIPTION

Figure 1:
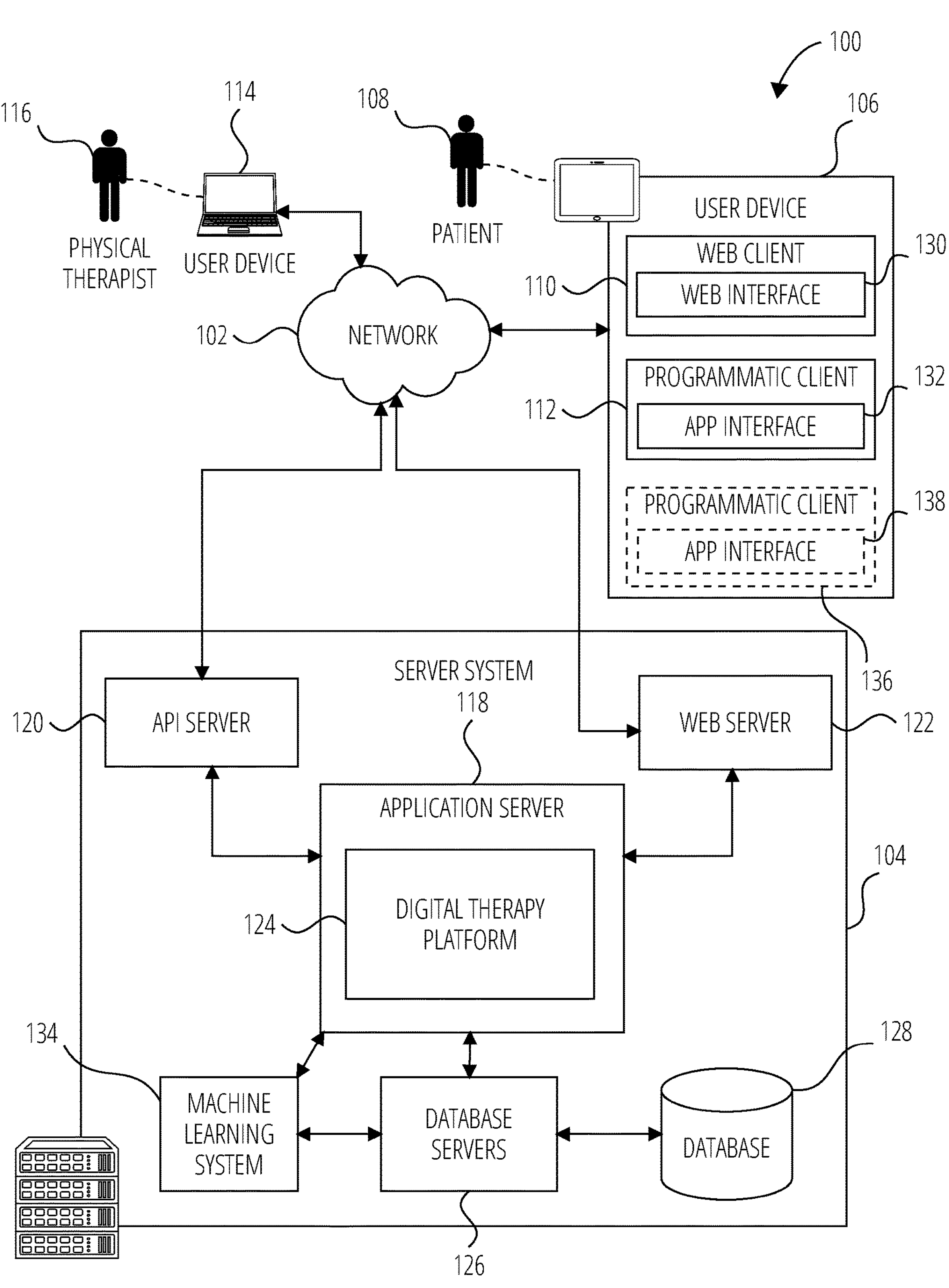
FIG. 1 diagrammatically illustrates a networked computing environment that includes a digital therapy platform, according to some examples.

While digital physical therapy technology may assist with patient rehabilitation or in providing relief from pain, as mentioned, it can be challenging to predict whether a particular patient will respond positively to therapy. As used herein, the term "responder" refers to a patient who responds positively to therapy, for example, by satisfying a predetermined improvement threshold upon conclusion of a digital physical therapy program. As an example, in the context of assessing pain associated with a MSK condition, the predetermined improvement threshold may be that, at the end of the digital physical therapy program, a patient has achieved a reduction of at least 30% in their pain level, as compared to a baseline, or reports a pain level below 4 points in the Numeric Pain Rating Scale (NPRS). If the patient does not satisfy the predetermined improvement threshold, the patient can be referred to as a non-responder.

The probability of a patient being a responder or non-responder may be influenced by several factors. The pathophysiology of pain may be multifactorial, influenced, for example, by biological, psychological, and social domains. Some factors, such as age, gender, or mental health, are not necessarily linked to the severity of the condition. It may be desirable to identify, prior to conclusion of a digital physical therapy program, that a patient is at risk (or at above-average risk) of being a non-responder. This can allow for interventions, such as adjustment of the digital physical therapy program to improve the prospects of achieving a significant improvement, or adjustment of a therapy workflow of a physical therapist (e.g., to prioritize a potential non-responder).

In some cases, a physical therapist may review each patient's progress manually and then attempt to predict whether the patient will be a responder. However, this can be a challenging task due to the multifactorial nature of pain. Furthermore, it may not be feasible, efficient, or cost-effective to require manual reviews of such vast amounts of data. Moreover, manual assessments can be subjective, leading to inconsistent flagging of patients.

Examples described herein provide digital physical therapy technology with functionality to flag a patient as a potential non-responder prior to conclusion of an intervention period, and to react to such a determination to implement interventions. Examples of the present disclosure provide an advanced operational tool, driven by artificial intelligence (AI), that is capable of flagging patients at risk of being non-responders and automatically adjusting one or more components of a digital physical therapy platform based on detection of a flag.

A system as described herein may collect data throughout a patient care journey (e.g., a digital physical therapy program designed to address a MSK condition, or some other digital care program), leveraging various data points, such as range of motion (ROM) data, patient-reported outcome measures (e.g., pain levels and fatigue levels), and digital therapy utilization data. The tool may utilize machine learning techniques to generate output data indicative of a predicted outcome of a digital physical therapy program. In some examples, the tool is configured to incorporate one or more temporal components that account for trends and complex time-dependent relationships, allowing for more accurate predictions.

In some examples, the tool is incorporated into a digital therapy platform. For example, a digital therapy platform may provide a cloud-based portal that is accessible by a physical therapist via a user device. The portal may be communicatively coupled to the tool to enable the physical therapist to utilize outputs generated by the tool. For example, by accessing patients' scores, flags, or other data at any stage of their journey, as generated by the tool, a physical therapist may be empowered to customize and refine their digital physical therapy programs accordingly. In some examples, a digital physical therapy program is automatically adjusted without intervention or input from a physical therapist or other user.

A method of the present disclosure may include accessing first data indicative of a baseline condition of a first user associated with a digital physical therapy program. The digital physical therapy program may be a structured plan or process for providing remote physical therapy to patients. Details of the digital physical therapy program may be stored in a database. For example, details of sessions, predetermined exercises, goals, or the like, may be stored in the database. The digital physical therapy program may include a plurality of sessions and may have a predetermined duration. For example, the digital physical therapy program may have a predetermined number of sessions, a predetermined duration, or both.

The baseline condition of the first user may describe one or more initial states of the first user at a time when the first user enrolled in the digital physical therapy program, or at a starting point of the digital physical therapy program. The baseline condition may be defined by various parameters, including fixed parameters and dynamic parameters. For example, the first data may include a baseline pain level of the first user, baseline ROM data of the first user, demographic data of the first user, clinical data of the first user, prescription data of the first user, behavioral data of the first user, social data of the first user, or current medication data of the first user. In some examples, the baseline condition, or an element thereof, may be used as a reference point to compare against patient outcomes.

The method may include collecting, for each of the plurality of sessions of the digital physical therapy program, second data indicative of at least one condition status of the first user. The second data may describe multiple condition statuses. Each condition status may be indicative of an aspect of the first user's health or condition at a particular point in time. For example, upon conclusion of each of a first session, a second session, and a third session of the digital physical therapy program, ROM data, a pain level, and/or a fatigue level may be recorded or collected for the respective session. One or more of the condition statuses may thus change or progress over time.

The first user has a first device that is used in the context of the digital physical therapy program. For example, the first device is used to track or monitor motion of the first user via one or more sensors during each of a plurality of sessions to automatically obtain at least some of the second data. As an example, the sensors may capture data that is processed to assess the first user's ROM during each session.

The first device may be a computing device that includes or is communicatively coupled to the one or more sensors. In some examples, the one or more sensors include at least one of a camera or a motion tracker. A sensor may be a hardware device coupled with, or incorporated into, a user device (e.g., the first device) that captures motion, health, exercise, biomechanical, or other data for use in the context of the digital therapy platform. Examples of sensors include wearable inertial sensors tracking body motion (e.g., inertial measurement units), a camera integrated into the first device, a camera separate from and communicatively coupled to the first device, and heart rate or other vital sign sensors.

In some examples, the digital therapy platform is a cloud-based platform. The first device may communicate with a server of the digital therapy platform, for example, to transmit at least some of the first data or at least some of the second data to the server. The server may communicate with the first device, for example, to transmit schedules, results, and exercise instructions (e.g., to provide a user interface that presents information and exercise instructions to the first user).

A condition status may represent the state of a patient's health or abilities at a given point of a digital physical therapy program after beginning the intervention. Examples of second data that may define or impact a condition status include ROM data automatically collected via the one or more sensors, the pain level of the first user, a fatigue level of the first user, or utilization data associated with the digital physical therapy program (e.g., to what extent the first user is participating in sessions, adhering to the digital physical therapy program, or interacting with a physical therapist, the presence or absence of incorrect movements, session duration, time of day when a session is performed, or day of week when a session is performed). The second data may thus include, for each session, automatically collected data and user-reported data.

The first data and the second data may be used to obtain, prepare, or generate input data to provide to a classifier component, such as a machine learning classifier or other machine learning model. The input data may include feature values for a plurality of features of the classifier component. In some examples, the classifier component is designed and trained to process data relating to one or more of demographic, clinical, prescription, and behavioral aspects of a patient (e.g., the first user), as described in greater detail elsewhere.

The classifier component may process the input data to generate output data indicative of a predicted outcome of the digital physical therapy program. In some examples, the classifier component comprises an algorithm that is trained on historical data to predict whether a patient associated with a digital physical therapy program will be a non-responder.

The classifier component may comprise a machine learning model trained using, for example supervised learning. In some examples, the classifier component comprises a tree-based ensemble classifier model trained using supervised learning, such as a random forest or gradient-boosting machine (such as Light Gradient Boosting Machine (LightGBM) or eXtreme Gradient Boosting (XGBoost)). Other machine learning models, such as neural networks, a Support Vector Machine, logistic regression, conditional inference trees, other types of decision trees, Nearest Neighbor (KNN), or Naive Bayes, may also be employed in the classifier component. The model may receive user-provided, collected, or generated data, or combinations thereof, to predict an outcome, as described in greater detail elsewhere.

As mentioned, the classifier component may process both first data that is indicative of the baseline condition and second data that is indicative of at least one condition status at subsequent points in time. For example, the classifier component may process temporal ROM features and utilization features up to a desired time point in the digital physical therapy program. These features, in combination with baseline values or scores, may allow the classifier component to generate predictions with improved accuracy. The classifier component may, alternatively or additionally, process data derived from the first data and/or second data, as is described in greater detail elsewhere.

The method may include detecting, based on the predicted outcome indicated by the classifier component, that the first user is predicted not to meet or satisfy a predetermined improvement threshold. This may include detecting that a final condition or final condition status of the first user, at the end of the digital physical therapy program, will not meet a predetermined improvement threshold.

The predetermined improvement threshold may define a target level of change for a patient health metric that signifies a successful digital physical therapy program outcome if met or exceeded. For example, the predetermined improvement threshold may be associated with a pain level of the first user (e.g., pain level at the end of an overall intervention period or program period). Examples of such improvements are a reduction of at least 20% in their pain level as compared to a baseline, a reduction of at least 30% in their pain level as compared to a baseline, a reduction of at least 40% in their pain level as compared to a baseline, a pain level of below 5 points in the NPRS, or a pain level of below 4 points in the NPRS.

In response to or otherwise based on detecting that the first user is predicted not to meet the predetermined improvement threshold, the digital therapy platform may automatically generate an alert associated with the first user. The method may include causing presentation of the alert at a second device associated with a second user administering the digital physical therapy program. The second user may be a physical therapist assigned to the first user or associated, in a database, with the digital physical therapy program of the first user.

The alert may be a notification or message generated by the digital therapy platform and presented within a physical therapist user interface to flag a change or detection relating to the first user's condition or risk profile. Examples of alerts include a warning that a patient is predicted not to meet an improvement threshold, an instruction that a patient should be prioritized, or an instruction to adjust a workflow or digital physical therapy programs as it relates to the patient.

As mentioned, the second data may include temporal data that is indicative of progress of the first user. Second data collected during or upon conclusion of respective sessions may be preprocessed to obtain values for certain features of the classifier component. For example, temporal ROM data may be engineered through latent growth curve models, structural network modeling, or one or more other longitudinal evolution models, with features of such models being used as classifier component inputs, as described in greater detail elsewhere. In some examples, a training data set is used to generate the at least one longitudinal evolution model. The at least one longitudinal evolution model is then applied to train the classifier component on at least a subset of the training data set.

The method may thus include preprocessing the second data from the plurality of sessions by applying at least one longitudinal evolution model to obtain preprocessed second data that is used downstream as input to the classifier component. The input data provided to the classifier component may, in such cases, include the preprocessed second data. For example, the first data provides values for a first subset of features of a machine learning classifier, and the preprocessed second data provides values for a second subset of features of the machine learning classifier.

In some examples, a longitudinal evolution model models historic patient data collected over multiple sessions to uncover trends, patterns, and latent trajectories that characterize how health metrics evolve over a treatment journey. Examples include growth curve models estimating trends in pain ratings, time series clustering to find distinct pain progression subgroups, and structural network analysis revealing connections between exercising ranges of motion. Examples of longitudinal evolution models may include one or more of a growth mixture model, a temporal structural network model, a repeated measures model, or multigroup growth model. In some examples, the least one longitudinal evolution model includes one or more of: a longitudinal evolution model (e.g., growth mixture model) that provides clusters of trajectories for pain, a longitudinal evolution model (e.g., growth mixture model) that provides clusters of trajectories for fatigue, or a longitudinal evolution model (e.g., temporal structural network model or growth curve) indicative of latent ROM.

The method may further include identifying a feature associated with the input data as a driver of the predicted outcome. The feature may be contained in the first data, the second data, or the preprocessed second data. The feature may be detected, for example, based on one or more prediction-explaining values obtained from execution of a prediction-explanation process or model interpretation process, such as one or more SHapley Additive explanation (SHAP) values or one or more Local Interpretable Model-agnostic Explanations (LIME) values.

For example, the system may automatically generate prediction-explaining values, such as SHAP values, to identify which feature, or features, had the highest relative contributions to the predicted outcome. One or more features identified in this manner may be designated as the drivers of the predicted outcome. The one or more drivers may be stored in a database in association with the first user. In some examples, the alert indicative of the predicted outcome may be presented at the second device with an indication of the one or more drivers of the predicted outcome. Prediction-explaining values may thus be automatically generated or updated for each patient, or for each inference, to determine the most relevant drivers.

The classifier component may be configured to generate a prediction after a predetermined number of sessions has been completed. For example, the method may include detecting that a predetermined number of sessions has been completed, and generating the predicted outcome automatically upon detecting that the predetermined number of sessions has been completed, prior to conclusion of the digital physical therapy program.

The predetermined number of sessions may depend on the use case. For example, the predetermined number of sessions may be between two and twelve sessions (e.g., four sessions or five sessions). In some examples, the classifier component is specifically trained to generate output data indicative of the predicted outcome based on input data covering the predetermined number of sessions.

The method may include generating, for the second user, a therapy workflow comprising one or more actions for the digital physical therapy program associated with the first user. Details of the therapy workflow may be stored in a database in association with the second user. The therapy workflow may be automatically adjusted based on the predicted outcome. The therapy workflow or the adjusted therapy workflow may be presented at the second device.

The therapy workflow may be presented in a user interface, such as within a dashboard or portal delivered through the digital therapy platform. The dashboard or portal may be used by a physical therapist to track patient conditions or status over time, to automate reports profiling risks, to assign educational content or exercises, or the like.

In some examples, the automatic adjustment of the therapy workflow includes assigning a priority indicator to the first user and causing presentation of the priority indicator at the second device, the priority indicator being presented in a user interface that includes at least part of the therapy workflow. For example, the first user may be automatically transferred to a list of priority patients of the physical therapist. The physical therapist may then be presented with the list of priority patients, for example, together with an indication of one or more drivers associated with each priority patient. Different subsets of drivers may be linked to different patients.

The output data generated by the classifier component may include a likelihood score. In some examples, the system detects that the final condition of the first user is predicted not to meet the predetermined improvement threshold if the likelihood score satisfies an alert threshold (e.g., reaches or exceeds the alert threshold). For example, where the classifier component generates a score of between 0 and 1, the alert threshold may be set at 0.7. If the score exceeds 0.7 for the first user, the system automatically classifies the first user as at risk of or likely to be a non-responder.

The operations of the method may include collecting, subsequent to generation of an initial predicted outcome by the classifier component, third data for one or more additional sessions of the digital physical therapy program. At least some of the third data may be automatically obtained via the one or more sensors. The method may then further include generating, using the classifier component and based at least on the third data, updated output data comprising an updated likelihood score. The updated likelihood score may be applied to determine whether the predicted outcome has changed. For example, a machine learning classifier may process a fresh set of input data that includes the third data to determine a new predicted outcome. As an example, the initial predicted outcome may be generated after four sessions, yielding a score of 0.65, which is below the alert threshold, while the subsequent predicted outcome is generated after five sessions, yielding a score of 0.72, which is above the alert threshold. In such a case, the system would only flag the first user as a non-responder upon generation of the subsequent predicted outcome.

Various types of digital physical therapy programs may be supported by the digital therapy platform described herein. In some examples, the digital physical therapy program comprises a plurality of exercises designed to treat a MSK condition (e.g., LBP) in the first user.

In some examples, a motion tracking system comprises a user device of the first user (e.g., the first device) and, optionally, one or more trackers. The motion tracking system may also include a server component associated with the digital therapy platform. Operations described herein may be performed by one or more components of such a motion tracking system.

In some examples, a digital therapy system comprises the user device of the first user, a user device of the second user (e.g., the second device), and the digital therapy platform (e.g., a cloud-based server providing the digital therapy platform). Operations described herein may be performed by one or more components of such a digital therapy system.

Examples described herein may address or alleviate one or more technical problems or system limitations. A tool as described herein may improve the functioning of digital physical therapy technology by enabling accurate prediction, prior to conclusion of a digital physical therapy program, of whether a patient will be a responder or non-responder. This may improve the utility and range of functionality of digital physical therapy technology and thereby facilitate wider adoption thereof.

In some cases, raw patient data, such as pain surveys and ROM metrics collected during sessions, provide high-dimensional, noisy snapshots that obscure important temporal patterns predictive of patient outcomes. By providing a system that automatically applies techniques or models as described herein, such as longitudinal evolution models including growth mixture models or temporal structural network models, latent features can be distilled from the raw data that characterize changes over time. This enables a system to track informative trends in patient trajectories and automatically feed inputs that account for those trends into predictive algorithms.

Sophisticated machine learning models, such as neural networks, may require significant computational resources to train or use, and may not always lend themselves to easy interpretation. Examples described herein utilize more lightweight models, such as tree-based ensemble machine learning classifiers, providing computational efficiency while generating highly useful predictive models that users can understand on a feature level.

As mentioned, current clinical workflows may rely on manual inspection of patient data. This does not scale effectively or efficiently across large volumes of patient data and may not allow for real-time notifications when risks are detected. Examples described herein provide a system that automatically generates alerts and updates therapy workflows based on predicted outcomes. In this way, a significantly more scalable and efficient decision support tool can be provided, for example, to augment existing workflows.

When the effects in this disclosure are considered in aggregate, one or more of the methodologies described herein may obviate a need for certain efforts or resources that otherwise would be involved in providing useful digital therapy technology. Computing resources used by one or more machines, databases, or networks may be more efficiently utilized or even reduced, for example, as a result of automatically generated predictions, as a result of downstream application of engineered features, or as a result of an overall reduction in computational load associated with model training or inference. Examples of such computing resources may include one or more of processor cycles, network traffic, memory usage, graphics processing unit (GPU) resources, data storage capacity, power consumption, and cooling capacity.

FIG. 1 is a diagrammatic representation of a networked computing environment 100 in which some examples of the present disclosure may be implemented or deployed. One or more servers in a server system 104 provide server-side functionality via a network 102 to a networked device, in the example form of a user device 106 that is accessed by a first user in the example form of a patient 108. A web client 110 (e.g., a browser) or a programmatic client 112 (e.g., an "app") may be hosted and executed on the user device 106. In some examples, the user device 106 executes further web clients or programmatic clients, such as the programmatic client 136 shown in broken lines in FIG. 1.

The one or more servers in the server system 104 also provide server-side functionality via the network 102 to a user device 114 of a second user in the example form of a physical therapist 116. Although not shown in FIG. 1, the user device 114 may include a web client or a programmatic client similar to the web client 110 or programmatic client 112 (or the programmatic client 136) of the user device 106.

An Application Programming Interface (API) server 120 and a web server 122 provide respective programmatic and web interfaces to components of the server system 104. An application server 118 hosts or provides a digital therapy platform 124, which may also be referred to as a digital therapy system, and which includes components, modules, or applications.

The user device 106 and the user device 114 can each communicate with the application server 118, for example, via the web interface supported by the web server 122 or via the programmatic interface provided by the API server 120. It will be appreciated that, although only a single user device 106 of the patient 108 and a single user device 114 of the physical therapist 116 is shown in FIG. 1, a plurality of other user devices may be communicatively coupled to the server system 104 in some examples. For example, multiple patients may use their respective user devices to access the digital therapy platform 124, and multiple physical therapists may use their respective user devices to access the digital therapy platform 124.

Further, while certain functions are described herein as being performed at either a user device (e.g., web client 110 or programmatic client 112) or the server system 104, the location of certain functionality either within a user device or the server system 104 may be a design choice. For example, it may be technically preferable to deploy particular technology and functionality within the server system 104 initially, but to migrate this technology and functionality to a programmatic client at a later stage (e.g., when the user device has sufficient processing capacity).

The application server 118 is communicatively coupled to one or more database servers 126, facilitating access to one or more information storage repositories (e.g., a database 128). In some examples, the database 128 includes storage devices that store information to be processed or transmitted by the digital therapy platform 124.

The application server 118 accesses application data (e.g., application data stored by the database servers 126 or database 128) to provide one or more applications to the user device 106 and the user device 114 (e.g., via a web interface 130 or an app interface 132). For example, and as described further below according to examples and with specific reference to FIGS. 2-5, the application server 118, using the digital therapy platform 124, may provide one or more digital therapy applications that include functionality to enable automatic generation of predictions of whether patients, such as the patient 108, will be responders or non-responders in the context of a digital physical therapy program.

The digital therapy platform 124 may provide the digital therapy application, or multiple digital therapy applications, to be accessible via the user device 106 or the user device 114. For example, the patient 108 may access a user portal of the digital therapy application to utilize various functionality, such as consulting virtually with the physical therapist 116, receiving a customized digital physical therapy program, receiving details of exercises to perform, and reviewing educational content, while the physical therapist 116 may access a therapist portal of the digital therapy application to utilize various functionality, such as consulting virtually with the patient 108, accessing a therapy workflow, and managing patients. Exemplary functions of the digital therapy platform 124 are further described with reference to FIG. 2 and FIG. 3.

Where multiple digital therapy applications are provided, different aspects of digital therapy may be provided via the respective applications. In one non-limiting example, a first application (e.g., the programmatic client 112) is a mobile application that provides an app interface (e.g., the app interface 132) for educational videos, cognitive behavioral therapy (CBT), and a communication channel with physical therapists, while a second application (e.g., the programmatic client 136) is a tablet application that provides access to exercises and an app interface (e.g., the app interface 138) for such purposes. The digital therapy application is referred to herein primarily as a single application for ease of reference and to facilitate understanding of aspects described herein. It will, however, be appreciated that, where this disclosure may refer to a single "digital therapy application" having certain functions, such functions may be performed by a single application or distributed across multiple applications. The digital therapy application, or applications, may be mobile applications, tablet applications, web applications, combinations thereof, or other types of applications.

To access the digital therapy application provided by the digital therapy platform 124, a user may create an account or access an existing account with a service provider associated with the server system 104 (e.g., a digital health services provider). The patient 108 or the physical therapist 116 may, in some examples, access the digital therapy application using a dedicated programmatic client (e.g., the programmatic client 112 and/or 136), in which case some functionality may be provided client-side and other functionality may be provided server-side.

Data stored in the database 128 may include various motion data, exercise data, and user data, such as demographic information, clinical history, and longitudinal records collected from the patients' user devices as well as through interactions with assigned physical therapists. It is noted that any biometric data or personally identifiable information (PII) is captured, collected, or stored only upon user approval and deleted on user request. Further, such data may be used for very limited purposes and only those purposes authorized by a user. To ensure limited and authorized use of biometric information or PII, access to this data is restricted to authorized personnel only, if at all. In addition, appropriate technical and organizational measures are implemented to ensure the security and confidentiality of this sensitive information.

The server system 104 may further host a machine learning system 134. The machine learning system 134 may be used to implement one or more aspects of a machine learning pipeline. For example, the machine learning system 134 may include components enabled to train relationship or prediction models based on historic patient data, attend to feature explainability functions, and serve inferences. Various aspects of machine learning pipelines and other AI-related features are described elsewhere, including with reference to FIG. 5.

One or more of the application server 118, the database servers 126, the API server 120, the web server 122, the digital therapy platform 124, or part thereof, may each be implemented in a computer system, in whole or in part, as described below with respect to FIG. 7. In some examples, third-party applications can communicate with the application server 118 via the programmatic interface provided by the API server 120 (or via another channel). For example, a third-party application may support one or more features or functions on a website or platform hosted by a third party, or may perform certain methodologies and provide input or output information to the application server 118 for further processing or publication. For example, the application server 118 may utilize functionality of machine learning models that are hosted by servers external to the server system 104.

The network 102 may be any network that enables communication between or among machines, databases, and devices. Accordingly, the network 102 may be a wired network, a wireless network (e.g., a mobile or cellular network), or any suitable combination thereof. The network 102 may include one or more portions that constitute a private network, a public network (e.g., the Internet), or any suitable combination thereof.

Figure 2:
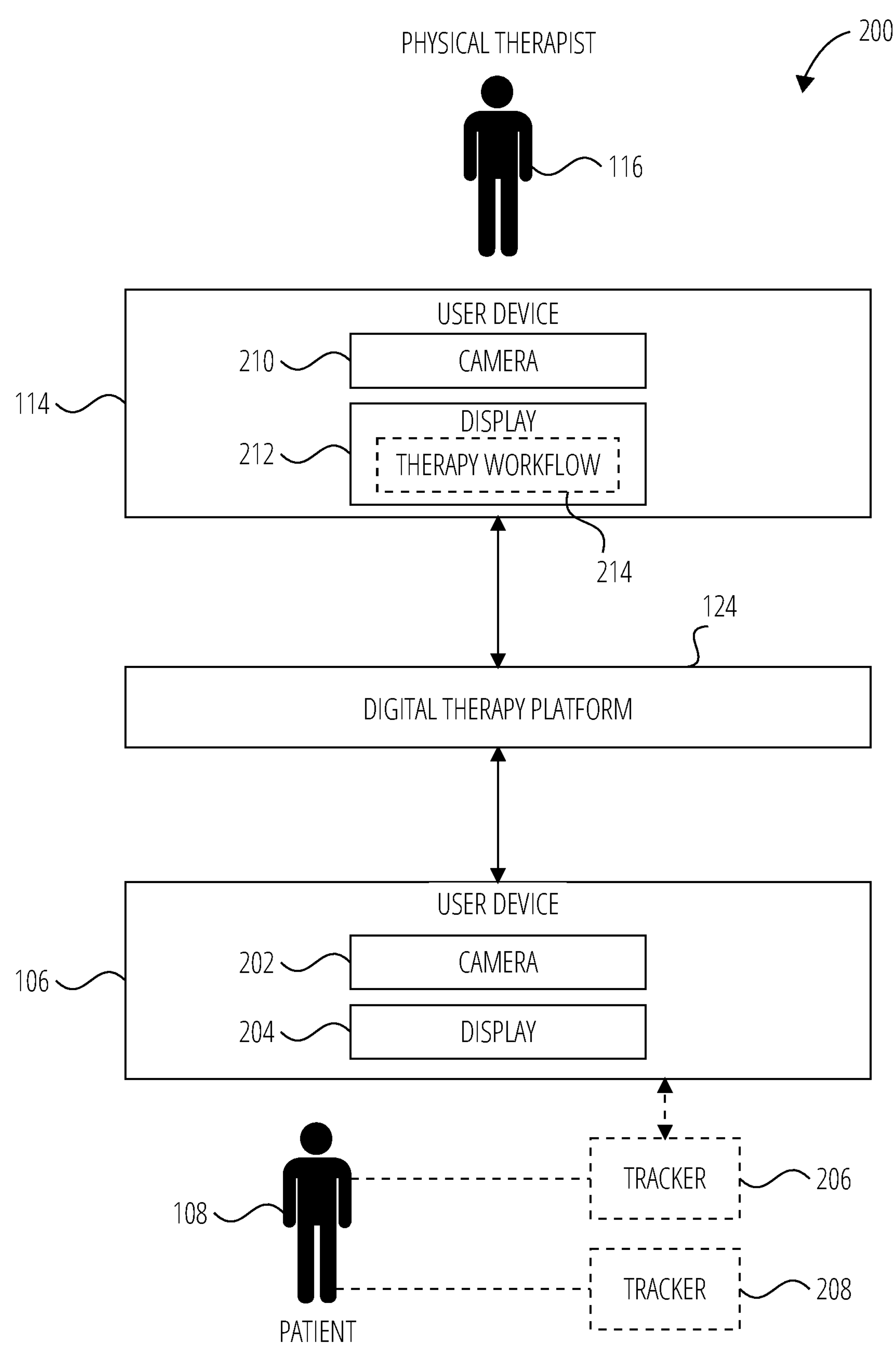
FIG. 2 diagrammatically illustrates interactions between a user device of a physical therapist, a cloud-based digital therapy platform, and a user device of a patient, according to some examples.

FIG. 2 shows an interaction diagram 200 depicting interactions between a user device of a physical therapist, the digital therapy platform 124 of FIG. 1, and a user device of a patient, according to some examples. In FIG. 2, the user device 114 of the physical therapist 116 of FIG. 1 and the user device 106 of the patient 108 of FIG. 1 are shown for ease of reference. It will be appreciated that similar interactions may be performed with other user devices connected to the digital therapy platform 124. It will further be understood that only a few selected components of the user device 106 and the user device 114 are shown in FIG. 2 to describe certain functionality, and that the user device 106 and the user device 114 may include numerous other components.

As discussed with reference to FIG. 1, both the user device 106 and the user device 114 are computing devices that can communicate with the digital therapy platform 124 (e.g., by accessing a digital therapy application). The user device 106 and the user device 114 may, for example, be mobile phones, tablets, personal computers, or combinations thereof.

The user device 106 includes, or is connected to, a camera 202 and a display 204. The user device 106 further includes at least one processor, at least one memory, and a communication module (not shown) for communicating with the digital therapy platform 124 and one or more other devices. The camera 202 may capture images or video content of the patient 108 performing exercises to allow tracking of user motion via computer vision techniques. For example, identification of anatomical landmarks, measurement of distances, and tracking of body parts may be performed using any computer vision techniques known in the art and they all fall within the scope of the present disclosure. Such computer vision techniques are not described in this document in order not to obscure the invention, but, to name a few non-limiting exemplary digital libraries and algorithms, TensorFlow Pose estimation, MediaPipe Pose, and BlazePose by Google™, and the algorithm described in "Reconstructing 3D Human Pose from 2D Image Landmarks" are some possible computer vision techniques to this end.

The camera 202 and other components of the user device 106 (e.g., microphone, loudspeaker, and communication modules) may also facilitate virtual consultations. The patient 108 may connect with the physical therapist 116 via the digital therapy platform 124, for example, to virtually consult with the physical therapist 116. The display 204 is used to provide a user interface of the digital therapy platform 124, such as a user interface of the digital therapy application.

The patient 108 may, for example, enter patient data, such as demographic information, clinical history, and symptoms (e.g., identification of painful zones and pain levels), and the data is then transmitted to the digital therapy platform 124. The digital therapy platform 124 may generate (e.g., automatically or with assistance from the physical therapist 116) a digital physical therapy program and make it available to the patient 108. For example, the digital therapy platform 124 may guide the patient 108 through an 8-week program or a 12-week program to treat or improve LBP or another MSK condition (the actual duration may vary or be dynamic, for example, based on patient condition, engagement, or recovery trajectory).

As mentioned, in some examples, the camera 202 can be used as a tracking sensor. Alternatively or additionally, the patient 108 may wear trackers 206, 208 on their body while performing the exercises forming part of the digital physical therapy program. Each tracker 206, 208 may include at least one sensor, for example, an inertial measurement unit. The inertial measurement unit of each tracker 206, 208 may include one or more inertial sensors selected from, for example, an accelerometer, a gyroscope, and a magnetometer.

Each tracker 206, 208 may further include at least one processor, at least one memory, and a wireless communications module for communicating with the user device 106. For example, each tracker 206, 208 may transmit advertisement packages, data packets with identification data (e.g., one or more identities or keys), data packets with measurements of inertial sensors, data packets with directions computed by the tracker, or combinations thereof. Each tracker 206, 208 may also receive data packets from the user device 106, for example, with tracking instructions. The trackers 206, 208 and/or the user device 106 may run sensor fusion algorithms, for example, to improve accuracy or correct errors in measurements.

Each tracker 206, 208 is adapted to be arranged on the body of the patient 108 so that the measurements thereof can be processed by the user device 106 or at the digital therapy platform 124, thereby providing a motion tracking sequence of the person. The trackers 206, 208 may be attached to body members of the person by means of an attaching device, such as straps, hook-and-loop fasteners, or other means. In some examples, the user device 106 and the trackers 206, 208 form part of a motion tracking kit provided to the patient 108. Each tracker 206, 208 may be powered by one or more batteries (e.g., a rechargeable battery).

The user device 106 may provide (or cause another device to provide) user-perceptible signals, such as exercise instructions or messages. For example, the display 204 and one or more loudspeakers may provide such user-perceptible signals. That is to say, the user device 106 may comprise one or more of visual output means, audio output means, vibrating means, or other means for providing user-perceptible signals in the form of sounds, vibration, animated graphics, etc.

For example, the display 204 of the user device 106 may show instructions and/or information to the patient 108 about the digital physical therapy program, such as predetermined movements that are to be performed by the patient 108, a list or representation of the body members that must have a tracker arranged thereon for a given exercise or motion tracking procedure, or results of the exercises performed by the patient 108. The user device 106 may thus provide a user interface to present instructions and/or information to the user and/or to receive inputs from the user. Any of these data can be transmitted to and/or received from another electronic device thanks to communicative couplings between the user device 114, the digital therapy platform 124, and the user device 106 (e.g., over the network 102 of FIG. 1). For example, the physical therapist 116 is able to receive the feedback at the user device 114 in a hospital (or other facility, such as an outpatient clinic, retirement home, or elderly care facility) so as to monitor the evolution or progress of the patient 108.

In some examples, one or more of the trackers 206, 208 may include a vital sign sensor. Examples of vital sign sensors include a respiration rate sensor, a body temperature sensor, a pulse rate sensor, or a combination of two or more thereof. In some examples, one or more of the trackers 206, 208, or the user device 106, also captures audio feedback via one or more audio sensors such that the audio feedback can be processed by the user device 106 or at the digital therapy platform 124 (e.g., to assist in determining the ease or difficulty experienced by the patient 108 in performing the exercises).

The physical therapist 116 may manage, edit, or track the digital physical therapy programs of various patients on the user device 114. For example, based on sensor measurements and user-reported feedback received with respect to the patient 108, the physical therapist 116 is able to adjust the digital physical therapy program by changing the difficulty of the movements or exercises, changing the number of repetitions thereof, prescribing new movements, and so forth. The patient 108 may also be provided with educational content (e.g., tailored educational content) and/or CBT via the digital therapy application.

The digital therapy platform 124 may provide for bidirectional communication with patients, for example, through a secure chat functionality available when the digital therapy application is installed on the user device 114 and the user device 106. This may enable, for example, virtual consultations between patients and physical therapists. The user device 114 also includes, or is connected to, a camera 210, for example, to facilitate such communications. As discussed with reference to the user device 106, the user device 114 also includes a display 212, at least one processor, at least one memory, and a communication module (not shown) for communicating with the digital therapy platform 124 and one or more other devices.

A therapy workflow 214 may be provided to the physical therapist 116 via a user interface presented on the display 212. For example, after authenticating into the digital therapy platform 124 (e.g., logging into the digital therapy application), the physical therapist 116 can access a therapy workflow 214 for their assigned patients (e.g., the patient 108) or for each assigned patient. The therapy workflow 214 may visualize baseline information, patient data over time, including, for example, measured ROM (e.g., using the trackers 206, 208 or computer vision techniques), self-reported pain ratings (e.g., a reported pain level after each session), utilization data, and/or fatigue levels. The therapy workflow 214 may provide predicted risk alerts (as described in greater detail below), next steps, tasks, and/or timeline views of exercise activity to assist the physical therapist 116. The therapy workflow 214 may also enable the physical therapist 116 to prescribe physical therapy interventions by selecting exercise regimens and scheduling follow-ups.

In some examples, the therapy workflow 214 is dynamically and automatically adjusted or updated to reflect the current state of the patient 108 based on the latest measurements and predictions. For example, the therapy workflow 214 may be adjusted to prioritize the patient 108 if the digital therapy platform 124 detects, upon completion of a specific session, that the patient 108 is predicted to be a non-responder.

Figure 3:
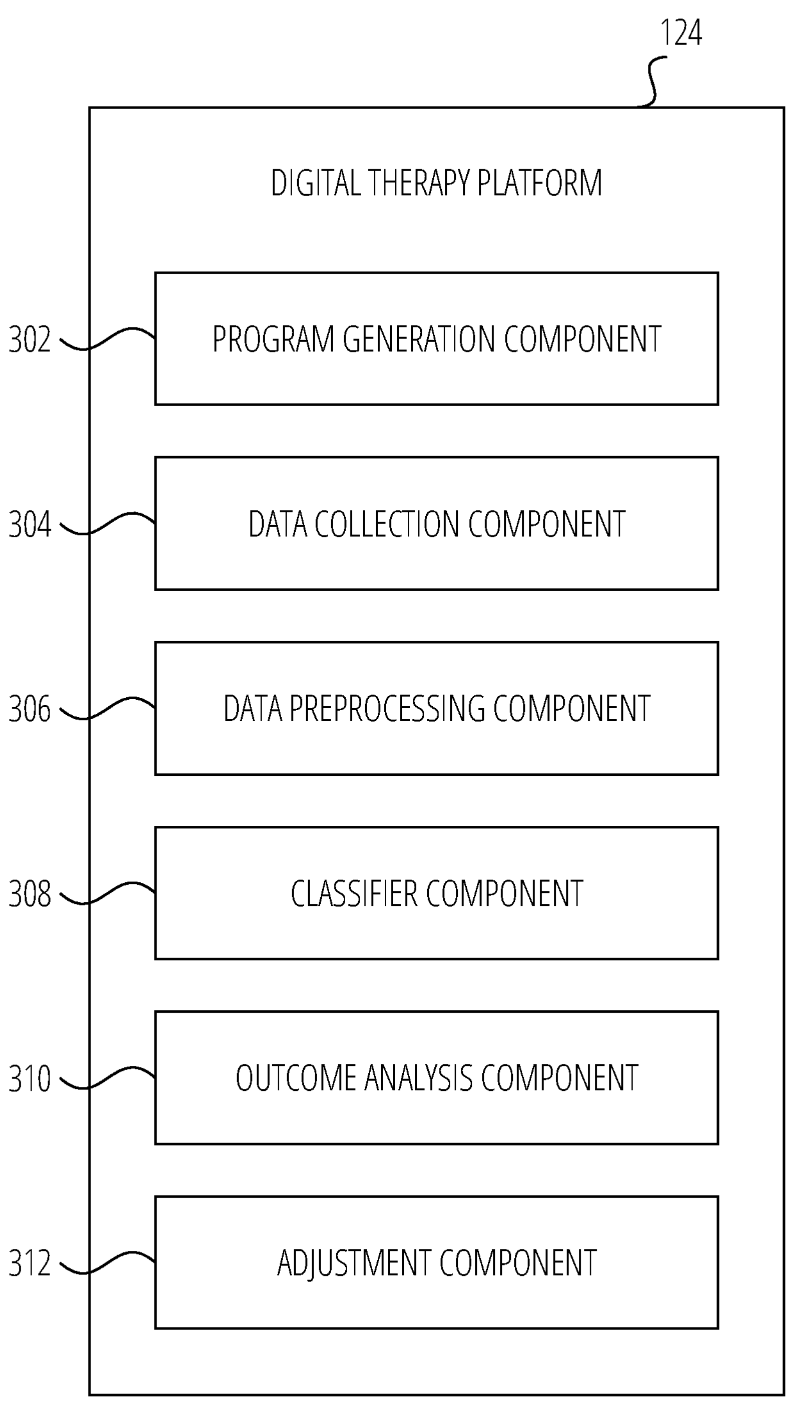
FIG. 3 is a block diagram illustrating components of a digital therapy platform, according to some examples.

FIG. 3 illustrates components of the digital therapy platform 124 of FIG. 1, according to some examples. The digital therapy platform 124 is shown to include a program generation component 302, a data collection component 304, a data preprocessing component 306, a classifier component 308, an outcome analysis component 310, and an adjustment component 312.

The program generation component 302 utilizes stored protocols (e.g., from the database 128) to enable the digital therapy platform 124 to create, or facilitate creation of, physical therapy interventions for each patient. For example, the program generation component 302 may generate a digital physical therapy program based on various data, such as personal or demographic information (e.g., age), clinical data, pain levels, and a type of condition. Further examples of data that may be utilized by the program generation component 302 are included in Table 1 below. In some examples, the program generation component 302 generates a default or suggested program which may be adjusted and/or personalized by the physical therapist 116 using the user device 114. The program generation component 302 may couple the digital physical therapy program with (or include therein) educational content sequences and consultations with a physical therapist. In some examples, the digital therapy application includes functionality to facilitate referrals, such as the physical therapist 116 initiating a referral of the patient 108 to a member of an extended care team (e.g., one or more of a dietician, psychologist, or sleep expert).

The digital physical therapy program may have a dynamic nature. For example, the physical therapist 116 may adjust or update the program over time depending on patient progression. In some examples, the digital therapy platform 124 monitors patient progress and performs at least some of these adjustments or updates automatically.

The data collection component 304 manages aggregating patient data from the user device 106 and/or other sources. Examples of collected data include initial information provided by the patient 108 prior to commencing with the digital physical therapy program, information provided by the physical therapist 116 via the user device 114 after consulting with the patient 108, and subsequent information collected once the patient 108 starts performing exercises (e.g., exercise performance metrics measured by motion trackers, patient-reported outcome survey results, and usage activity associated with the digital therapy application). The data collection component 304 may cause the data to be stored in the database 128. Further examples of data that may be collected or accessed by the data collection component 304 are included in Table 1 below.

The data preprocessing component 306 may prepare certain "raw" patient data, such as session-specific data collected by the data collection component 304, for effective analysis, model training, or inference. This may involve, for example, cleaning missing or outlying values in the data, imputing missing data, aligning data from disparate sources onto common timelines, distilling high-dimensional data into informative features, and transforming features onto comparable numerical scales. In some examples, engineered features are processed through longitudinal evolution models by the data preprocessing component 306. For example, temporal ROM data collected across different sessions may be processed through a temporal structural network model and/or latent growth curves. As another example, time-linked pain levels recorded up to a certain session (and possibly including a baseline pain level) can be processed through a growth mixture model to obtain clusters of pain trajectories. Such preprocessed data may then serve as input to other components, such as the classifier component 308 of the digital therapy platform 124.

The classifier component 308 implements one or more trained machine learning models that process input data to generate predictions related to digital physical therapy outcomes. For example, the classifier component 308 may implement a tree-based ensemble classifier model that is trained using supervised learning to generate output data indicative of whether a patient will be, or is predicted to be, a non-responder. The classifier component 308 may communicate with the machine learning system 134, for example, during model training, evaluation, or inference. In some examples, the classifier component 308 is hosted by the machine learning system 134 and communicates with the components of the digital therapy platform 124.

Table 2 below provides non-limiting examples of features of the machine learning classifier for an implementation in which a predicted outcome is generated after completion of the fourth session. All or a subset of these features may be utilized in examples of the present disclosure. Some features may also be included per exercise, for example. The features are intended to be illustrative and not exhaustive. For example, in some cases, hundreds of features may be utilized in the machine learning classifier. Examples of certain features, as well as the derivation or modeling of some of the features, are described with reference to FIG. 5.

The outcome analysis component 310 may consume and analyze output data generated by the classifier component 308. For example, the outcome analysis component 310 may check whether a likelihood score in the output data exceeds a predetermined alert threshold, which may also be referred to as a decision threshold. For example, the alert threshold may be set at 0.7 where the classifier component 308 generates a score of between 0 and 1 (with scores closer to 1 indicating a higher likelihood of being a non-responder). If the outcome analysis component 310 detects that the likelihood score exceeds the predetermined alert threshold, it may flag the patient (e.g., in the database 128), with the flag indicating that the patient (e.g., a final condition of the patient) is predicted not to meet a predetermined improvement threshold. For example, the flag may indicate that the patient is likely not to meet an improvement threshold associated with a pain level of the patient. The classifier component 308 may be trained based on the predetermined improvement threshold such that its output data can be analyzed in accordance with that same threshold.

The adjustment component 312 uses the outcome determinations from the outcome analysis component 310 to automatically adjust one or more aspects of the digital physical therapy program. The adjustment component 312 may generate and present alerts to the physical therapist and/or the patient. The adjustment component 312 may automatically adjust content of the digital physical therapy program (e.g., an exercise schedule or duration) and update the therapy workflow 214 of the associated physical therapist. In some cases, the adjustment component 312 generates or assigns a priority indicator to a patient who has been flagged as a potential non-responder. The adjustment component 312 may cause the therapy workflow 214 to be updated to include or present the priority indicator in association with the patient, thereby instructing the physical therapist to prioritize the patient. The adjustment component 312 may be configured to receive user input, e.g., from the user device 114 of the physical therapist 116, to validate adjustments or trigger further adjustments. For example, the adjustment component 312 may generate a suggested adjustment to the digital physical therapy program which is presented in the user interface on the user device 114. The physical therapist 116 can then provide user input to confirm, adjust, or deny such adjustments or modifications to the digital physical therapy program.

The adjustment component 312 may also cause one or more drivers of the predicted outcome to be presented, for example, in the user interface of the physical therapist. As described elsewhere, the digital therapy platform 124 may automatically identify one or more features as key contributors to a non-responder flag and cause those features to be communicated to the physical therapist for review (e.g., within the context of the therapy workflow 214 at the user device 114). The adjustment component 312 may also automatically update the therapy workflow 214 or the digital physical therapy program of a patient based on the one or more drivers (e.g., to automatically adjust an exercise schedule to improve a specific feature). As mentioned above, the physical therapist 116 may be enabled, via the user device 114, to validate or adjust updates generated or proposed by the adjustment component 312.

In some examples, at least some of the components shown in FIG. 2 or FIG. 3 are configured to communicate with each other to implement aspects described herein. Any one or more of the components described herein may be implemented using hardware (e.g., one or more processors of one or more machines) or a combination of hardware and software. For example, a component described herein may be implemented by a processor configured to perform the operations described herein for that component. Moreover, two or more of these components may be combined into a single component, or the functions described herein for a single component may be subdivided among multiple components. Furthermore, according to various examples and where applicable, components described herein may be implemented using a single machine, database, or device, or be distributed across multiple machines, databases, or devices.

TABLE 1

| Examples of data that may be used (at least in part) in a machine learning pipeline and/or at inference | | |
|---|---|---|
| Domain | Sub-domains | Description |
| Demographic | Individual characteristics | Information about gender, age, race/ethnicity, body mass index, and/or education level |
| | Geographical location | Urban or rural location and/or time zone |
| | Social deprivation | It may be assessed using publicly available indexes; examples are social deprivation index or area deprivation index. Social deprivation index was used in the example framework discussed below. |
| | Public health measures | Assessed using publicly available indexes; an example can be PLACES: Local Data for Better Health |
| | Work characteristics | Employment status and/or job type |
| Clinical | Condition | Information about condition diagnosis (e.g., MSK condition), anatomical pain region, presence of symptoms, chronicity, and/or past surgery. |
| | Pain | Pain intensity assessed by any patient reported outcome metric; examples can be the NPRS and/or the score of item 1 of Oswestry Disability Index (ODI). NPRS was used in the example framework discussed below. |
| | Functionality | Assessed by any patient reported outcome metric for disability. An example for low back can be ODI (0-100) considering the total score and the individual score of items 2-7 (this example was used in the example framework discussed below). |
| | Participation - Work | Assessed by any patient reported outcome metric for productivity impairment; an example can be the Work Productivity Impairment questionnaire for general health (WPAI) assessing overall work productivity, presenteeism, and absenteeism subscales (this example was used in the example framework discussed below). |
| | Participation - Social | Assessed by any patient reported outcome metric for non-work-related activities or quality of life; an example can be Work Productivity Impairment questionnaire for general health (WPAI) and scores of items 8, 9 and 10 of ODI (this example was used in the example framework discussed below). |
| | Biomechanics | Assessed by any metric for biomechanics. An example can be active ROM of prescribed exercises (e.g., time-series of mean active ROM over all repetitions of each prescribed exercise). In the example framework below, this metric was used over the first four sessions. |
| | Mental health | Assessed by any patient reported outcome metric for mental health; an example can be the General Anxiety Disorder 7-item scale (GAD-7) and the Patient Health 9-item Questionnaire (PHQ-9), considering the total score and the individual score for each item (this example was used in the example framework discussed below). |
| | Fear-avoidance | Assessed by any patient reported outcome metric for fear avoidance or pain catastrophization; an example can be the Fear-Avoidance Beliefs Questionnaire for Physical Activity (FABQ-PA), considering the total score and the individual score for each item (this example was used in the example framework discussed below). |
| | Surgery intent | Assessed by any patient reported outcome metric for surgery intent; an example can be the question "On a scale of 0 to 100, where 0 is not at all, and 100 is extremely interested, how interested are you in undergoing shoulder surgery in the next 12 months?" (this example was used in the example framework discussed below). |
| | Medication consumption | Considers analgesics and/or opioids intake |
| | Red flags | Presence of red flags identified during onboarding screening |

TABLE 1-continued

Examples of data that may be used (at least in part) in a machine learning pipeline and/or at inference

| Domain | Sub-domains | Description |
|---|---|---|
| Prescription | Support level | Includes support level perception assessed by the physical therapist interactions during the intervention |
| | Prescription-related variables | Includes exercise parameters (e.g., prescribed sessions frequency) prescribed by the physical therapy |
| | Acute exercise response | Pain felt during exercise sessions assessed by NPRS or any related patient reported outcome metric (NPRS was used in the example framework discussed below). |
| | Exercise intensity | Self-reported fatigue following the question "My fatigue during today's session?"(0-10) or any related patient reported outcome metric (the former question was used in the example framework discussed below). |
| Behavior | Enrollment aspects | Time period from enrollment until (1) onboarding and (2) first session |
| | Motivation | Patient individual goals with the intervention and/or session commitment |
| | Physical activity level | Physical activity habits |

TABLE 2

Examples of features of a machine learning model

| # | Feature |
|---|---|
| 1 | Pain at baseline (NPRS) |
| 2 | Gender |
| 3 | Acuity |
| 4 | Probability of belonging to pain trajectories cluster 1 |
| 5 | Probability of belonging to pain trajectories cluster 2 |
| 6 | Probability of belonging to pain trajectories cluster 3 |
| 7 | Probability of belonging to pain trajectories cluster 4 |
| 8 | Probability of belonging to pain trajectories cluster 5 |
| 9 | Probability of belonging to fatigue trajectories cluster 1 |
| 10 | Probability of belonging to fatigue trajectories cluster 2 |
| 11 | Probability of belonging to fatigue trajectories cluster 3 |
| 12 | Probability of belonging to fatigue trajectories cluster 4 |
| 13 | Probability of belonging to fatigue trajectories cluster 5 |
| 14 | Session commitment at onboarding |
| 15 | Time from onboarding to first session |
| 16 | Average pain during exercising - first session (NPRS) |
| 17 | Average pain during exercising - second session (NPRS) |
| 18 | Average pain during exercising - third session (NPRS) |
| 19 | Average pain during exercising - fourth session (NPRS) |
| 20 | Total time exercising - first session |
| 21 | Total time exercising - second session |
| 22 | Total time exercising - third session |
| 23 | Total time exercising - fourth session |
| 24 | Intake of prescribed medication |
| 25 | Latent ROM intercept |
| 26 | Latent ROM slope |
| 27 | Latent ROM curvature |
| 28 | Probability of belonging to non-responder class - ROM temporal structural network model |
| 29 | Probability of belonging to responder class - ROM temporal structural network model |
| 30 | Latent ROM - first session |
| 31 | Latent ROM - second session |
| 32 | Latent ROM - third session |
| 33 | Latent ROM - fourth session |
| 34 | Mean active ROM over all exercises - first session |
| 35 | Mean active ROM over all exercises - second session |
| 36 | Mean active ROM over all exercises - third session |
| 37 | Mean active ROM over all exercises - fourth session |

Figure 4:
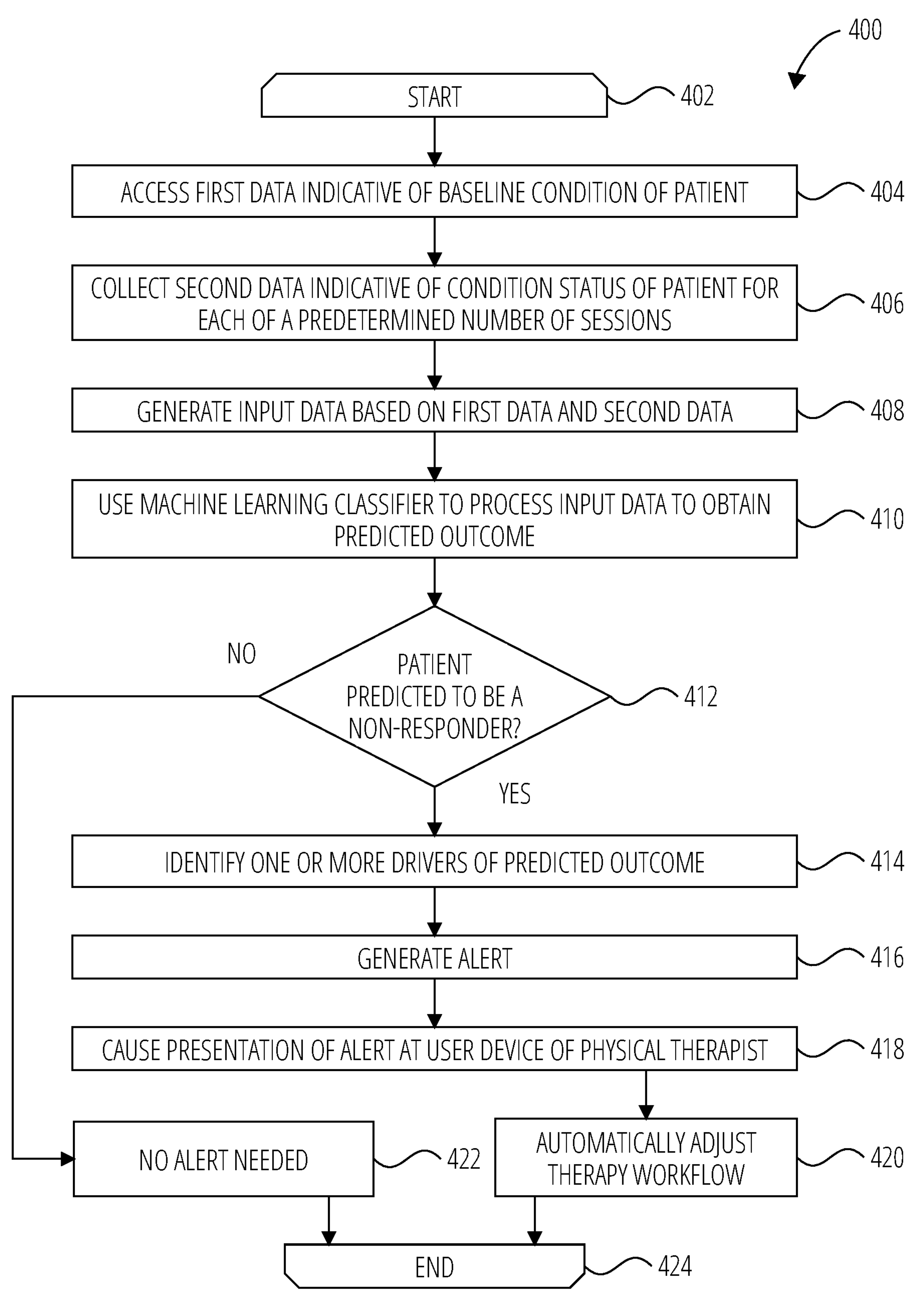
FIG. 4 is a flowchart illustrating a method suitable for automatically predicting an outcome of a digital physical therapy program upon conclusion of a predetermined number of sessions of the digital physical therapy program, according to some examples.

FIG. 4 is a flowchart illustrating a method 400 suitable for automatically predicting an outcome of a digital physical therapy program, according to some examples. Operations in the method 400 may be performed by the digital therapy platform 124, the user device 114 and/or the user device 106 using components (e.g., parts, modules, systems, or engines) described above with respect to FIGS. 1-3. Accordingly, by way of example and not limitation, the method 400 is described with reference to components described with respect to FIGS. 1-3. However, it shall be appreciated that at least some of the operations may be deployed on various other hardware configurations or be performed by similar components residing elsewhere.

The method 400 commences at opening loop element 402 and proceeds to operation 404, where the digital therapy platform 124 accesses first data indicative of a baseline condition of the patient 108. For example, where available, values associated with one or more of the data items included in Table 1 may be collected at baseline or otherwise prior to commencement of sessions. The patient 108 may use the user device 106 to input at least some of the first data and upload or transmit such first data to the digital therapy platform 124.

At operation 406, while a digital physical therapy program of the patient 108 is in progress, the digital therapy platform 124 collects second data indicative of at least one condition status of the patient 108 for each of a predetermined number of sessions (e.g., using the data collection component 304 of the digital therapy platform 124). For example, as the patient 108 performs physical therapy exercises, the trackers 206, 208 capture motion data (e.g., body kinematics) and transmit the motion data in real-time to the user device 106, which processes the data and uploads it to the digital therapy platform 124 where it is incorporated a longitudinal record for analysis. Alternatively or additionally, the user device 106 may use the camera 202 to capture motion of the patient 108 and analyze the motion using computer vision techniques (e.g., to determine ROM data for the patient 108 across different exercises).

In some examples, the predetermined number of sessions is four sessions, and the digital therapy platform 124 collects respective data associated with a first session, a second session, a third session, and a fourth session of the digital physical therapy program. Some of the data may be user-selected or user-provided, such as a pain level reported upon conclusion of each session via the user device 106. Other data may be automatically collected, such as ROM data obtained via one or more sensors during each session (as described above), or utilization data that indicates how the patient 108 is using the digital therapy platform 124 (e.g., how soon after onboarding the patient started with their sessions, the duration of each session, or the time between consecutive sessions).

At operation 408, input data is generated for the classifier component 308 of the digital therapy platform 124. At least some of the first data and/or second data may be used directly as input data, and at least some of the first data and/or second data may be preprocessed to generate input data. For example, temporal pain level data may be preprocessed through a growth mixture model to obtain probabilities of the patient 108 belonging to each of a plurality of clusters of pain trajectories. As another example, temporal ROM data may be preprocessed through a growth curve model to determine the probability of the patient 108 belonging to a non-responder class. These longitudinal evolution models are, in some examples, created using at least some of the training data set that is also used to train the classifier component 308, as described with reference to FIG. 5. The probabilities obtained from one or more longitudinal evolution models may then be used as input data that are fed to the classifier component 308 (e.g., to supplement the "raw" ROM, pain, and/or fatigue data points).

Other examples of preprocessing include determining time periods, such as the time between onboarding and the first session. In some examples, preprocessing is performed automatically by the data preprocessing component 306 of the digital therapy platform 124.

The method 400 proceeds to operation 410, where the input data is provided to the classifier component 308 (e.g., an ensemble machine learning classifier, as described elsewhere) to cause generation of output data indicative of a predicted outcome of the digital physical therapy program. The input data may, for example, include values for at least a subset of the features in Table 2. Where the predetermined number of sessions is four sessions, operation 410 is performed by the digital therapy platform 124 automatically upon conclusion of the fourth session. In some examples, the classifier component 308 processes baseline condition data, temporal data relating to each session, and other "fixed" data, such as demographic information, to generate the output data.

As discussed, the output data may include a score, such as a likelihood score, in some examples (e.g., a score between 0 and 1 that indicates how likely the patient 108 is to be a non-responder by the end of the intervention period). In such cases, the model score is subjective to the threshold for setting the binary label. Alternatively or additionally, the output data may include a direct label prediction.

At decision operation 412, the digital therapy platform 124 checks whether the patient 108 is predicted to be a non-responder. For example, where the classifier component 308 generates a likelihood score, the outcome analysis component 310 checks whether the likelihood score meets or exceeds an alert threshold. In another example, where the classifier component 308 generates a label that indicates "responder" or "non-responder" without a likelihood or probability score, the digital therapy platform 124 merely checks the label.

The definition of a non-responder may depend on the manner in which the classifier component 308 was trained. For example, the classifier component 308 may be trained on labeled training data in which patients were flagged as non-responders if they did not experience at least a 30% pain reduction as measured by the NPRS, or if their final pain level was above a threshold level. Accordingly in some examples, a predetermined improvement threshold utilized in the training of the classifier component 308 is that the pain level of the patient is at or below a predetermined pain threshold upon conclusion of the digital physical therapy program, or that the patient has a predetermined reduction in the pain level upon conclusion of the digital physical therapy program. It is noted that, in other examples, one or more metrics other than pain level may be utilized to assess patient improvement. For example, a predetermined improvement in disability level, or a predetermined improvement in ROM data, may be utilized. These metrics may be utilized as alternatives or in addition to pain levels.

If, at decision operation 412, the patient 108 is predicted to be a non-responder, the digital therapy platform 124 identifies one or more drivers of the predicted outcome at operation 414. For example, as explained elsewhere, the digital therapy platform 124 may generate and/or analyze SHAP values to identify which features of the machine learning classifier made the biggest contributions to the non-responder prediction. For example, the digital therapy platform 124 may identify "total time spent exercising during the third session" and "total time spent exercising during the fourth session" as two main drivers in a particular case (inference).

The digital therapy platform 124 then generates an alert at operation 416. The alert is, for example, a notification indicating that the patient 108 has been flagged as at risk of being a non-responder. The alert may be intended to notify a user that, for example, a final condition or final condition status of the patient is predicted not to meet a predetermined improvement threshold associated with a pain level of the patient 108.

At operation 418, the alert is presented at the user device 114 of the physical therapist 116 assigned to the patient 108. The alert may be presented in a user interface of the digital therapy application (e.g., as part of the therapy workflow 214). In some examples, the one or more drivers are also communicated to the physical therapist 116 at the user device 114. For example, the physical therapist 116 may be informed, via a user interface provided by the digital therapy platform 124, that key reasons for the patient 108 being classified as a potential non-responder include sub-optimal "total time spent exercising during the third session" and "total time spent exercising during the fourth session." In some cases, the features identified as drivers may be presented in the user interface together with their values (e.g., to allow the physical therapist 116 to easily identify how much time the patient 108 spent exercising in the aforementioned sessions). This may allow the physical therapist 116 to understand key concerns associated with the patient 108, implement suitable adjustments, or make relevant recommendations to the patient 108 via the digital therapy platform 124 (e.g., by adjusting their digital physical therapy program or initiating a virtual consultation or secure chat).

In some examples, and as is the case in FIG. 4, the method 400 proceeds to operation 420, where the therapy workflow 214 of the physical therapist 116 is automatically adjusted based on the predicted outcome. For example, in response to the outcome analysis component 310 detecting, after conclusion of the fourth session, that the patient 108 is at risk of being a non-responder, the adjustment component 312 of the digital therapy platform 124 generates a priority indicator (e.g., a flag or other visual indicator) and displays it in association with patient data of the patient 108 in the therapy workflow 214 at the user device 114. The digital therapy platform 124 may also update one or more tasks assigned to the physical therapist 116 in the therapy workflow 214 such that the patient 108 is prioritized (e.g., by moving the name of the patient 108 to a "priority patient list" in the therapy workflow 214) and display updated tasks in the user interface.

In some examples, the digital therapy platform 124 automatically updates the digital physical therapy program based on the determined driver or drivers of the predicted outcome. For example, where sub-optimal "total time spent exercising during the third session" and "total time spent exercising during the fourth session" were detected, the digital therapy platform 124 may automatically update the digital physical therapy program to instruct the patient 108, via the user device 106, to perform a fifth session of a longer duration. As mentioned, the digital therapy platform 124 may enable the physical therapist 116 to provide user input, for example, to input, validate, or modify an update to the digital physical therapy program.

It will be appreciated that various other automatic adjustments may be performed (e.g., by the adjustment component 312) with respect to the therapy workflow 214 or other components provided by the digital therapy platform 124 in order to respond effectively to the output data received from the classifier component 308.

On the other hand, if, at decision operation 412, the digital therapy platform 124 determines that the patient 108 is not predicted to be a non-responder, no alert is needed at that stage. For example, if the likelihood score generated by the classifier component 308 is below an alert threshold, the digital therapy platform 124 may automatically refrain from generating an alert (operation 422). The digital therapy platform 124 may also record the determination made (e.g., record that the patient 108 was assessed and not flagged as a possible non-responder). The method 400 concludes at closing loop element 424.

In some cases, if, at decision operation 412, the digital therapy platform 124 determines that the patient 108 is not predicted to be a non-responder, the digital therapy platform 124 may automatically transmit a notification to the user device 114 of the physical therapist 116 to indicate that the patient 108 is predicted to be a responder. For example, when the physical therapist 116 views patient data of the patient 108 in the user interface of the physical therapist portal, the patient data is presented by the digital therapy platform 124 together with a "responder" indicator to communicate the predicted outcome.

Figure 5:
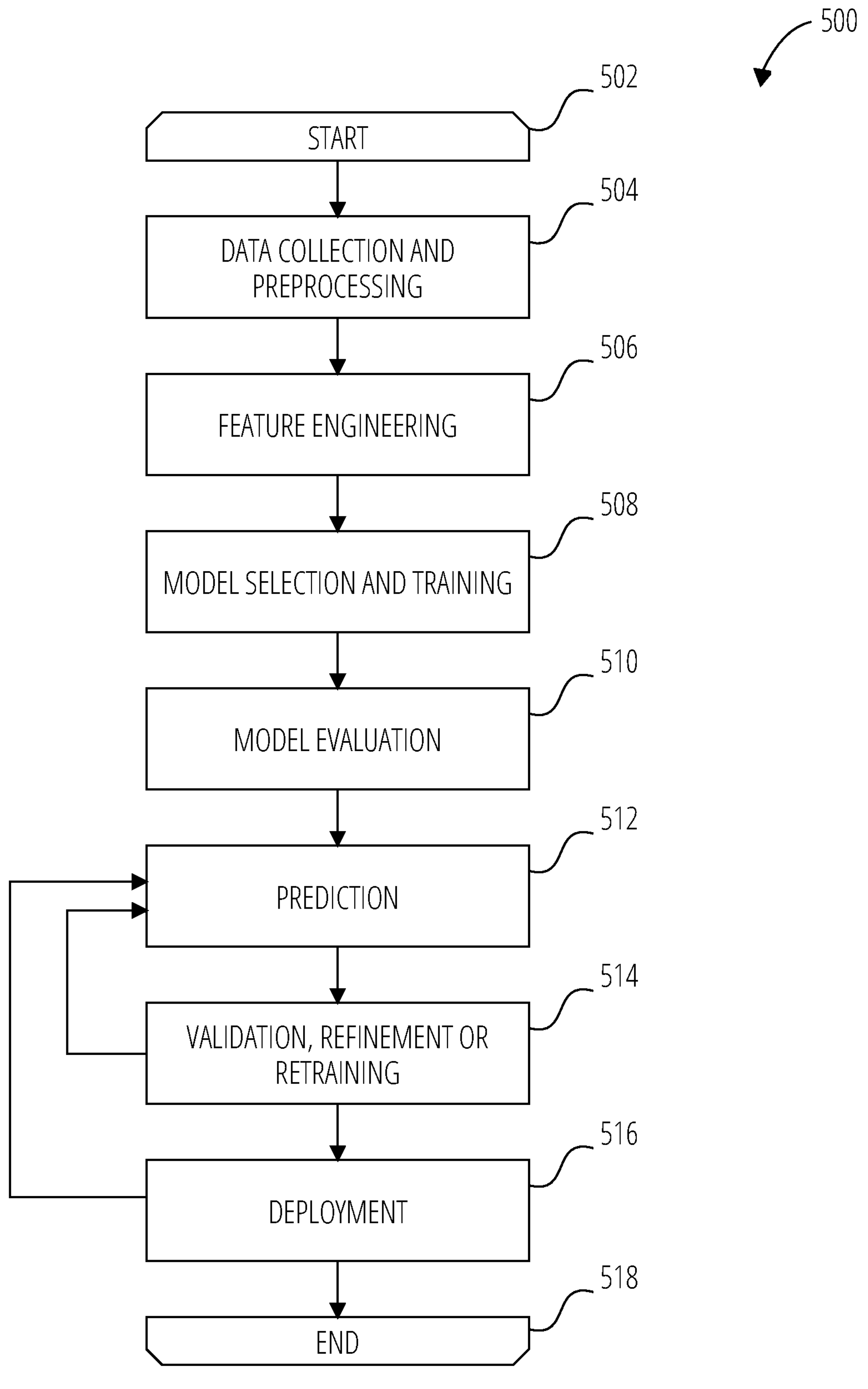
FIG. 5 is a flowchart illustrating a machine learning pipeline, according to some examples.

FIG. 5 is a flowchart depicting a machine learning pipeline 500, according to some examples. The machine learning pipeline 500 may be used to generate a trained model, such as a trained machine learning classifier (e.g., implemented by the classifier component 308 of FIG. 3). One or more aspects of the machine learning pipeline 500 may be implemented using the machine learning system 134 of FIG. 1.

The generation of a trained model may include multiple phases between an opening loop element 502 and a closing loop element 518 that form part of the machine learning pipeline 500, including, for example, the following phases illustrated in FIG. 5:

- Data collection and preprocessing 504: This phase may include acquiring, cleaning and/or performing initial processing of data to ensure that it is suitable for use in the machine learning model or for feature engineering purposes. This phase may also include removing duplicates, handling missing values, and/or converting data into a suitable format. Training data may be obtained or finalized at the end of data collection and preprocessing 504.
- Feature engineering 506: This phase may include selecting and transforming the training data set, or portions thereof, to create features that are useful for predicting a target variable. Feature engineering may include (1) receiving features (e.g., as structured or labeled data in supervised learning) and/or (2) identifying features (e.g., unstructured or unlabeled data for unsupervised learning) in the training data. Training data may be modified based on the outcomes of feature engineering.
- Model selection and training 508: This phase may include selecting an appropriate machine learning algorithm and training it on the preprocessed and/or feature-engineered data. This phase may further involve splitting the data into training and testing sets, using cross-validation to evaluate the model, and/or tuning hyperparameters to improve performance.
- Model evaluation 510: This phase may include evaluating the performance of a trained model on a separate testing data set. This phase can help determine if the model is overfitting or underfitting and determine whether the model is suitable for deployment.
- Prediction 512: This phase involves using the trained model to generate predictions on new, unseen data.
- Validation, refinement or retraining 514: This phase may include updating a model based on feedback generated from the prediction phase, such as new data, new requirements, or user feedback.
- Deployment 516: This phase may include integrating the trained model into a more extensive system or application, such as the digital therapy platform 124 of FIG. 1. This phase can involve setting up APIs, building a user interface, and ensuring that the model is scalable and can handle large or relatively large volumes of data. It will be appreciated that the trained model may be continuously or periodically updated, making the machine learning pipeline 500 an iterative or partially iterative process, as indicated by the arrows in FIG. 5.

A detailed, non-limiting example of a framework (referred to below as the "example framework") that was utilized to generate a trained model will now be described. The example framework or a framework similar thereto may, for example, be used to generate a model used by the classifier component 308 of FIG. 1, for use in the digital therapy platform 124 of FIG. 1. The details of the example framework are primarily provided for illustrative purposes, and a person of ordinary skill in the art will appreciate that it may be possible to utilize other techniques, data, features, values, models, structures, or processes to generate a trained model for use in a digital therapy platform as described herein.

Operations forming part of the example framework may be performed by the digital therapy platform 124, the user device 114 and/or the user device 106 using components (e.g., parts, modules, systems, or engines) described above with respect to FIGS. 1-3. Accordingly, by way of example and not limitation, aspects of the example framework are described with reference to components described with respect to FIGS. 1-3. However, it shall be appreciated that at least some of the operations may be deployed on various other hardware configurations or be performed by similar components residing elsewhere.

At a high level, the example framework was designed to provide a trained model that assesses the likelihood of a patient being a non-responder upon completion of a predetermined session of a digital physical therapy program. In the case of the example framework, the fourth session was selected as the predetermined session. The example framework provides that, if this likelihood surpasses a predefined decision threshold, an alarm or alert is triggered on the digital therapy platform 124, supporting either an automatic adjustment, a physical therapist's reevaluation of the digital physical therapy program, or both. In this way, one or more technical limitations associated with digital therapy platforms may be overcome or at least alleviated.

In the example framework, the digital physical therapy program was focused on treating patients suffering from LBP. It will, however, be appreciated, that various aspects of the example framework may be applied in the context of other conditions, such as other MSK conditions. The digital physical therapy program was multimodal, involving exercise sessions, education, and CBT, being managed and/or administered remotely by a physical therapist. The digital physical therapy program spanned about 12 weeks for each patient (with the actual duration depending on patient condition, engagement, or recovery trajectory), the aim being to develop a technical solution that can perform early detection (shortly after the fourth session) of patients who are at risk of not achieving significant improvements in terms of pain alleviation or reduction. The example framework was also designed to enable detection of factors that are strong predictors (e.g., drivers) of a specific outcome, such that those factors may be automatically surfaced and utilized by the digital therapy platform 124 to further improve the functionality of digital physical therapy technology.

A set of patients for which patient data was obtained to generate a training data set each participated in their own digital physical therapy program. After enrolling through a dedicated website, patients filled out a baseline condition form with information regarding their demographic and clinical characteristics. Each patient was entitled to choose their physical therapist from a pool of certified physical therapists. Subsequently, an onboarding video-call was performed where the physical therapist collected additional data to define the baseline condition, such as the medical history, and also worked to set up goals and desired outcomes from the intervention, collaboratively with the patient.

Each patient received a kit at home, which consisted of a device in the form of a dedicated tablet with a mobile application installed thereon (this is an example of the user device 106 of FIG. 1 with the digital therapy application installed thereon), as well as motion trackers if needed (e.g., where computer vision was not utilized for body tracking). The device provides real-time video and audio biofeedback on exercise execution through the use of the motion trackers, and a cloud-based portal that enables asynchronous and remote monitoring by the assigned physical therapist. Each physical therapist could access a therapist portal via their own device (e.g., the user device 114 of FIG. 1). Using the user interface provided by the portal, the physical therapist can assess patient-specific needs. Three exercise sessions per week were recommended and performed autonomously at patients' convenience. Patients were also provided with tailored education content and CBT, based on current clinical guidelines and prior research.

For ease of understanding, further details of the example framework are set out below with reference to the operations 504-516 of the machine learning pipeline 500 of FIG. 5.

Data Collection and Preprocessing 504:

Data for a cohort of patients with LBP was collected from a data warehouse based on a specific timeframe. Data encompassing demographics, clinical characteristics, ROM, and usability were retrieved. Additionally, publicly available data sets describing socioeconomic deprivation and public health were incorporated into the data set.

In the present disclosure, "usability" data is also referred to as "utilization" data, and refers, for example, to the manner in which a patient used or uses the digital therapy platform. Examples of usability data may include, for a particular session, existence or absence of movement errors, time on session, number of exercises, number of sets and repetitions and the type of exercise, and messages exchanged with the physical therapist. More generally, usability data may indicate to what extent the patient is participating in sessions, adhering to the digital physical therapy program, or interacting with a physical therapist. Furthermore, usability data may indicate how soon after onboarding the patient started with their sessions or the time between consecutive sessions.

The following inclusion criteria were applied to the cohort: usability data until the fourth session; pain level equal to or greater than 4 on the NPRS at baseline, considering a 7-day recall period; and at least one pain reassessment during the intervention. The following labels were applied: patients who did not experience a pain reduction of at least 30% or had a pain level at or above 4 on the NPRS at the end of the intervention period were categorized as non-responders, and labeled as "1."

The initial, cleaned data set contained 6,125 samples, 2,172 of which were label positives, and 433 features. The data set was divided into training/validation and test data sets using a 70/30 split, where the 30% were sampled from the most recent entries of the data set.

Feature Engineering 506:

The training set (70% of the samples, as indicated above) was used to create models for feature engineering. The feature engineering process took advantage of latent information of longitudinal data. Temporal data, such as recovery trajectories, may provide a higher accuracy in prognostic prediction than traditional diagnosis, and such trajectories were incorporated into the example framework to generate the final trained model.

Specifically, to add to the variables in Table 1, data collected until the fourth exercise session including active ROM and self-reported pain and fatigue during exercises, as well as data until the $27^{th}$ session from pain (NPRS) reassessments were used to develop models for feature engineering.

(a) Feature Engineering Using ROM Data

ROM data was computed using temporal structural network modeling and latent growth curve analysis to derive variables that represent ROM longitudinal evolution. The probability of a patient belonging to either the responder or non-responder networks were used as features of the model. The multigroup latent growth curve ROM model separately provided a latent representation of ROM changes for responders and non-responders.

The multigroup latent growth curve depicts the underlying distributions of responders and non-responders and was derived from observed ROM measurements across all four timepoints. These four latent representations of ROM at each time point were then used to estimate individual trajectories. At participant-level, an intercept, slope, and curve estimates as well as the ROM at each timepoint (t) were calculated and used as features of the model. In Equations 1 and 2 below, $ROM^{g}_{t}$ is a latent ROM variable at each time point t; I, S, and C are latent intercept, slope, and curve parameters defining longitudinal trajectories of ROM per class g; $rom^{g}_{ti}$ is a measured ROM variable, i, at time, t, for class g; $\mu_{ti}$ is a vector of means of each ROM variable at each time point; $\lambda_{ti}$ is a vector of factor loadings relating observed ROM scores to latent ROM scores; and $e^g_t$ and $e^g_t$ represent model error and measurement error respectively.

$$ROM_t^g = I^g + S^g t + C^g t^2 + e_t^g \quad \text{(Equation 1)}$$

$$rom_{ti}^g = \mu_{ti} + \lambda_{ti} ROM_t^g + \epsilon_t^g \quad \text{(Equation 2)}$$

Referring to Equations 1 and 2, the observed measurements were used to construct a new variable that exists as the underlying cause of participants having different ROM scores, with Equation 2 specifically showing that the variable is modeled and tracked over time.

Two temporal structural network models based on the temporal covariance matrix of the mean ROM data of each exercise over the four sessions were calculated for responders and non-responders, presenting significantly different covariance matrices (P<0.001). The chi-square difference values obtained from the comparison between the individual covariance matrix and the covariance matrix of each class (Equation 3) were added to the model as two features. In Equation 3 below, Σ is a model expected covariance matrix; I is an identity matrix; B is a parameter matrix; and ϕ is a diagonal matrix containing error variance components. Equation 3 thus shows how the network is constructed as a model expected covariance matrix.

$$\sum = \left[(I - B)^T \phi^{-1} (I - B)\right]^{-1} \quad \text{(Equation 3)}$$

(b) Feature Engineering Using Fatigue and Pain Data

Distinct clusters of trajectories of fatigue during exercise sessions were created using growth mixture modeling. For each participant, the probability of belonging to a distinct cluster was computed and used as a feature for the model. Bayesian information criteria (BIC) selected five distinct fatigue clusters of trajectories. It was noted that clusters starting with higher levels of fatigue were also those with worse clinical presentations.

Pain (NPRS) clusters of trajectories were investigated following the above-described method (growth mixture modeling and BIC). Similarly, five clusters were found that followed three trends: rapidly improving pain; gradually improving pain; and persistent pain. For each participant, the probability of belonging to these clusters was used as features of the model, after computing their expected pain over the intervention via Multiple Imputation by Chained Equation (MICE).

The individual probability of a patient being assigned to each recovery trajectory class was calculated via likelihood ratios (Equation 4), yielding five probabilities per participant per variable. In Equation 4 below, $x_t$ is a vector of observations at time t; G is the total number of mixture clusters assessed; $I^g$, $S_g$, and $C^g$ are latent intercept slope and curve parameters for each cluster; $p_g$ denotes a vector of probabilities of belonging to a cluster; and $e_t$ is an error term.

$$x_t = \sum_{g=1}^{G} p_g\left(I^g + S^g t + C^g t^2\right) + e_t \quad \text{(Equation 4)}$$

After feature engineering, the initial number of candidate variables was reduced to 309 after implementing feature selection, which involved identifying high correlations between variables and employing recursive feature elimination. More specifically, for pairs of numerical features that had a Spearman correlation coefficient higher than 0.90, one feature was randomly removed. Subsequently, recursive feature elimination was performed after hyperparameter optimization.

Model Selection and Training 508:

At a high level, model selection and training involved investigating tree-based binary classifiers optimized using the receiver operating curve area under the curve (ROC-AUC) as the target metric. Precision and recall curves were employed as evaluation metrics, and model explainability was assessed using SHAP values. Tree-based models were chosen for tool development as they do not require normalization or data scaling, and may be less vulnerable to missing data, while also often allowing easier interpretability of the model's decisions. These models may thus offer more interpretability with less training time being needed. Furthermore, ensembles were preferable as they tend to outperform single-trees.

Three tree-based ensemble methodologies were tested on the test set to assess the best performance for non-responder detection. LightGBM and XGBoost presented the highest ROC-AUC, while random forest presented a slightly lower ROC-AUC. These results were obtained using a ten-fold cross-validation strategy in the training set. Best parameters for the final model were chosen using ROC-AUC as target variable. The precision-recall AUC for LightGBM was similar to XGBoost and superior to random forest.

For each fold in the cross-validation, Synthetic Minority Oversampling TEchnique (SMOTE) was applied to oversample the training data of both classes until 5000 samples per class. SMOTE is a complex form of oversampling that artificially creates new data by using nearest neighbors technique. With the best hyperparameters, a final model was trained (LightGBM was selected based on the above results) using the full 70% of training data, which was not used for validation.

Model Evaluation 510:

Final model performance was assessed by evaluating the test data set and measuring the ROC-AUC and precision-recall AUC. An F1 score was also computed to assess model predictive power at a threshold of 0.5.

Prediction 512:

The final model, trained using the example framework, can generate output data indicative of whether a patient will be a non-responder.

Validation, Refinement or Retraining 514:

Global feature importance was based on absolute mean SHAP values. In the trained model of the example framework, the features included in Table 3 were identified as the top 15 features influencing the predicted outcome. The values in Table 3 are those generated prior to zero SHAP value feature elimination and retraining, which is discussed below.

TABLE 3

Mean average SHAP values for top 15 features in a model trained using the example framework

| Feature | Mean average SHAP |
|---|---|
| Probability of belonging to pain trajectories 1 | +2.85 |
| Pain (NPRS) at baseline | +1.55 |

TABLE 3-continued

Mean average SHAP values for top 15 features in a model trained using the example framework

| Feature | Mean average SHAP |
|---|---|
| Probability of belonging to pain trajectories 3 | +1.4 |
| Probability of belonging to pain trajectories 4 | +1.28 |
| Probability of belonging to pain trajectories 2 | +0.79 |
| Intake of prescribed medication | +0.48 |
| Probability of belonging to pain trajectories 5 | +0.36 |
| Probability of belonging to fatigue trajectories 1 | +0.21 |
| Session commitment at onboarding | +0.19 |
| Acuity | +0.19 |
| Gender | +0.16 |
| Probability of belonging to fatigue trajectories 2 | +0.16 |
| Total time exercising - third session | +0.14 |
| Average pain during exercising - fourth session (NPRS) | +0.14 |
| Time from onboarding to first session (days) | +0.14 |
| Sum of other features | +8.66 |

SHAP is a feature attribution method used to compute the importance of a given feature to the outcome of the model. It is noted that, in the model trained using the example framework, many top features had a temporal component, including the pain trajectory probabilities obtained from the longitudinal evolution models generated for pain and fatigue. The pertinence of using temporal components, in at least some implementations, was further reinforced by other factors, such as the ranking of average pain at the fourth session in the top features of model explainability, and also the ranking of total time exercising in the third session in the top features. For all four sessions, the relationship between average pain and treatment outcome demonstrated similar behavior, where a pain level of above 4 (NPRS) was associated with a higher likelihood to be non-responder. This illustrates that technical advantages, such as improved prediction accuracy, can be obtained by training a model so as to incorporate temporal components.

In the example framework, variables with zero feature attribution (zero SHAP value) were deemed not to contribute to the model output and were therefore removed, followed by subsequent model retraining using the remaining features.

Deployment 516:

A model trained based on the example framework can be used as, or as part of, a classifier component (e.g., the classifier component 308) in a digital therapy system, such as the system depicted in FIG. 1 (e.g., a system providing the digital therapy platform 124). The trained model may assist in providing a technical solution to limitations of digital therapy technologies in providing high predictive accuracy to identify, at an early stage and prior to program completion, patients at high risk of not attaining clinically meaningful change in pain.

Figure 6:
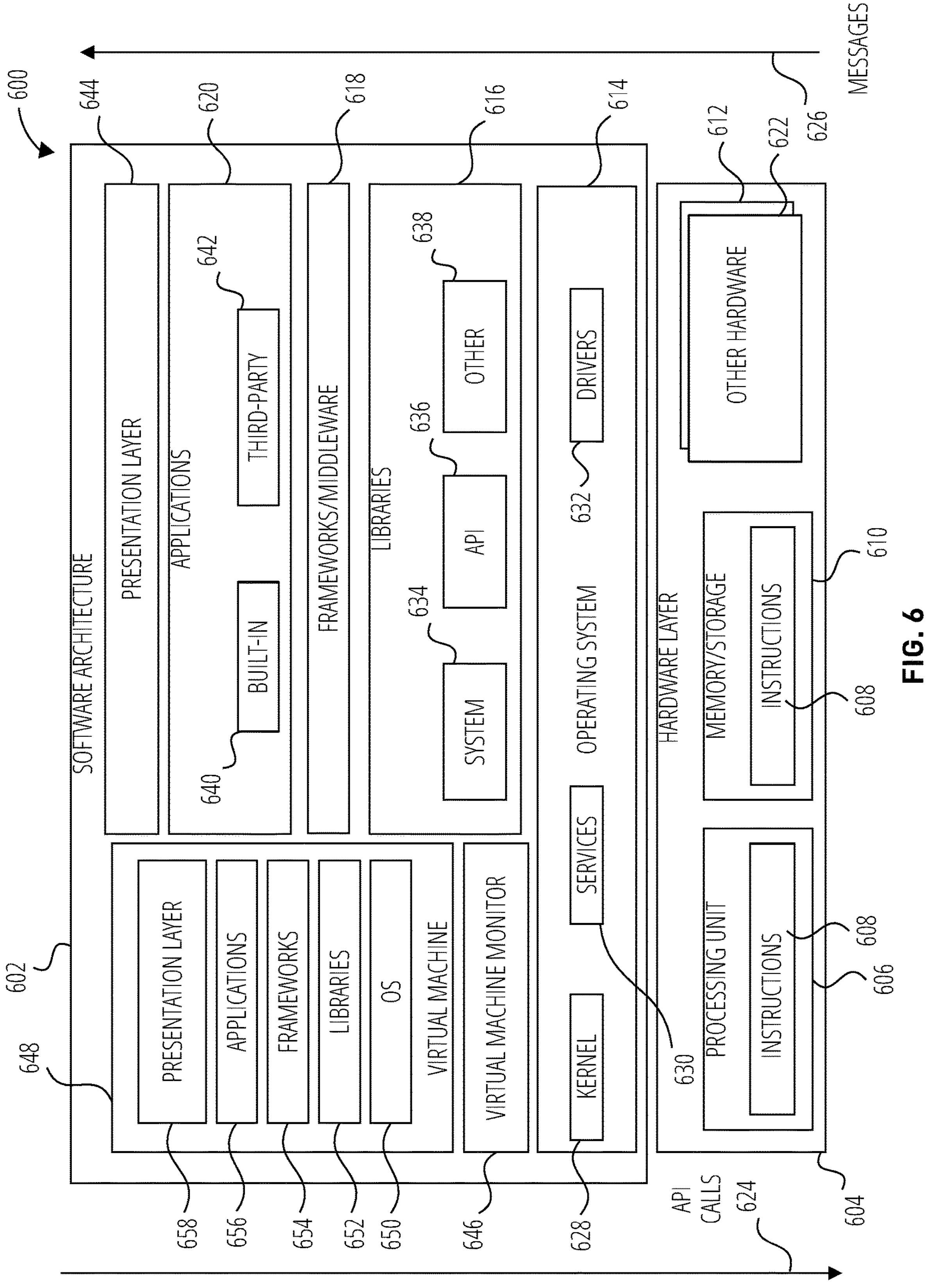
FIG. 6 is a block diagram showing a software architecture for a computing device, according to some examples.

FIG. 6 is a block diagram 600 showing a software architecture 602 for a computing device, according to some examples. The software architecture 602 may be used in conjunction with various hardware architectures, for example, as described herein. FIG. 6 is merely a non-limiting illustration of a software architecture, and many other architectures may be implemented to facilitate the functionality described herein. A representative hardware layer 604 is illustrated and can represent, for example, any of the above referenced computing devices. In some examples, the hardware layer 604 may be implemented according to the architecture of the computer system of FIG. 7.

The representative hardware layer 604 comprises one or more processing units 606 having associated executable instructions 608. Executable instructions 608 represent the executable instructions of the software architecture 602, including implementation of the methods, modules, subsystems, and/or components, and so forth described herein and may also include memory and/or storage modules 610, which also have executable instructions 608. Hardware layer 604 may also comprise other hardware as indicated by other hardware 612 and other hardware 622 which represent any other hardware of the hardware layer 604, such as the other hardware illustrated or described as part of a computing device or computing system described herein.

In the architecture of FIG. 6, the software architecture 602 may be conceptualized as a stack of layers where each layer provides particular functionality. For example, the software architecture 602 may include layers such as an operating system 614, libraries 616, frameworks/middleware layer 618, applications 620, and presentation layer 644. Operationally, the applications 620 or other components within the layers may invoke calls, such as API calls 624, through the software stack and access a response, returned values, and so forth illustrated as messages 626 in response to the calls. The layers illustrated are representative in nature and not all software architectures have all layers. For example, some mobile or special purpose operating systems may not provide a frameworks/middleware layer 618, while others may provide such a layer. Other software architectures may include additional or different layers.

The operating system 614 may manage hardware resources and provide common services. The operating system 614 may include, for example, a kernel 628, services 630, and drivers 632. The kernel 628 may act as an abstraction layer between the hardware and the other software layers. For example, the kernel 628 may be responsible for memory management, processor management (e.g., scheduling), component management, networking, security settings, and so on. The services 630 may provide other common services for the other software layers. In some examples, the services 630 include an interrupt service. The interrupt service may detect the receipt of an interrupt and, in response, cause the software architecture 602 to pause its current processing and execute an interrupt service routine (ISR) when an interrupt is accessed.

The drivers 632 may be responsible for controlling or interfacing with the underlying hardware. For instance, the drivers 632 may include display drivers, camera drivers, Bluetooth® drivers, flash memory drivers, serial communication drivers (e.g., Universal Serial Bus (USB) drivers), Wi-Fi® drivers, near-field communication (NFC) drivers, audio drivers, power management drivers, and so forth, depending on the hardware configuration.

The libraries 616 may provide a common infrastructure that may be utilized by the applications 620 or other components or layers. The libraries 616 typically provide functionality that allows other software modules to perform tasks in an easier fashion than to interface directly with the underlying operating system 614 functionality (e.g., kernel 628, services 630, or drivers 632). The libraries 616 may include system libraries 634 (e.g., C standard library) that may provide functions such as memory allocation functions, string manipulation functions, mathematic functions, and the like. In addition, the libraries 616 may include API libraries 636 such as media libraries (e.g., libraries to support presentation and manipulation of various media format such as MPEG4, H.264, MP3, AAC, AMR, JPG, PNG), graphics libraries (e.g., an OpenGL framework that may be used to render two-dimensional and three-dimensional graphic content on a display), database libraries (e.g., SQLite that may provide various relational database functions), web libraries (e.g., WebKit that may provide web browsing functionality), and the like. The libraries 616 may also include a wide variety of other libraries 638 to provide many other APIs to the applications 620 and other software components/modules.

The frameworks/middleware layer 618 may provide a higher-level common infrastructure that may be utilized by the applications 620 or other software components/modules. For example, the frameworks/middleware layer 618 may provide various graphic user interface (GUI) functions, high-level resource management, high-level location services, and so forth. The frameworks/middleware layer 618 may provide a broad spectrum of other interfaces, such as APIs, that may be utilized by the applications 620 or other software components/modules, some of which may be specific to a particular operating system or platform.

The applications 620 include built-in applications 640 or third-party applications 642. Examples of representative built-in applications 640 may include, but are not limited to, a contacts application, a browser application, a book reader application, a location application, a media application, a messaging application, or a game application. Third-party applications 642 may include any of the built-in applications as well as a broad assortment of other applications. In a specific example, the third-party application 642 (e.g., an application developed using the Android™ or iOS™ software development kit (SDK) by an entity other than the vendor of the particular platform) may be mobile software running on a mobile operating system such as iOS™, Android™, Windows® Phone, or other mobile computing device operating systems. In this example, the third-party application 642 may invoke the API calls 624 provided by the mobile operating system such as operating system 614 to facilitate functionality described herein.

The applications 620 may utilize built in operating system functions (e.g., kernel 628, services 630, or drivers 632), libraries (e.g., system libraries 634, API libraries 636, and other libraries 638), and frameworks/middleware layer 618 to create user interfaces to interact with users of the system. Alternatively, or additionally, in some systems, interactions with a user may occur through a presentation layer, such as presentation layer 644. In these systems, the application/module "logic" can be separated from the aspects of the application/module that interact with a user.

Some software architectures utilize virtual machines. In the example of FIG. 6, this is illustrated by virtual machine 648. A virtual machine creates a software environment where applications/modules can execute as if they were executing on a hardware computing device. A virtual machine is hosted by a host operating system (operating system 614) and typically, although not always, has a virtual machine monitor 646, which manages the operation of the virtual machine as well as the interface with the host operating system (e.g., operating system 614). A software architecture executes within the virtual machine 648 such as an operating system 650, libraries 652, frameworks/middleware 654, applications 656 or presentation layer 658. These layers of software architecture executing within the virtual machine 648 can be the same as corresponding layers previously described or may be different.

Certain examples are described herein as including logic or a number of components, modules, or mechanisms. Modules or components may constitute either software modules/components (e.g., code embodied (1) on a non-transitory machine-readable medium or (2) in a transmission signal) or hardware-implemented modules/components. A hardware-implemented module/component is a tangible unit capable of performing certain operations and may be configured or arranged in a certain manner. In examples, one or more computer systems (e.g., a standalone, client, or server computer system) or one or more hardware processors may be configured by software (e.g., an application or application portion) as a hardware-implemented module/component that operates to perform certain operations as described herein.

In various examples, a hardware-implemented module/component may be implemented mechanically or electronically. For example, a hardware-implemented module/component may comprise dedicated circuitry or logic that is permanently configured (e.g., as a special-purpose processor, such as a field programmable gate array (FPGA) or an application-specific integrated circuit (ASIC)) to perform certain operations. A hardware-implemented module/component may also comprise programmable logic or circuitry (e.g., as encompassed within a general-purpose processor or another programmable processor) that is temporarily configured by software to perform certain operations. It will be appreciated that the decision to implement a hardware-implemented module/component mechanically, in dedicated and permanently configured circuitry, or in temporarily configured circuitry (e.g., configured by software) may be driven by cost and time considerations.

Accordingly, the term "hardware-implemented module" or "hardware-implemented component" should be understood to encompass a tangible entity, be that an entity that is physically constructed, permanently configured (e.g., hardwired), or temporarily or transitorily configured (e.g., programmed) to operate in a certain manner or to perform certain operations described herein. Considering examples in which hardware-implemented modules/components are temporarily configured (e.g., programmed), each of the hardware-implemented modules/components need not be configured or instantiated at any one instance in time. For example, where the hardware-implemented modules/components comprise, a general-purpose processor configured using software, the general-purpose processor may be configured as respective different hardware-implemented modules/components at different times. Software may accordingly configure a processor, for example, to constitute a particular hardware-implemented module/component at one instance of time and to constitute a different hardware-implemented module/component at a different instance of time.

Hardware-implemented modules/components can provide information to, and receive information from, other hardware-implemented modules/components. Accordingly, the described hardware-implemented modules/components may be regarded as being communicatively coupled. Where multiple of such hardware-implemented modules/components exist contemporaneously, communications may be achieved through signal transmission (e.g., over appropriate circuits and buses that connect the hardware-implemented modules/components). In examples in which multiple hardware-implemented modules/components are configured or instantiated at different times, communications between such hardware-implemented modules/components may be achieved, for example, through the storage and retrieval of information in memory structures to which the multiple hardware-implemented modules/components have access. For example, one hardware-implemented module/component may perform an operation, and store the output of that operation in a memory device to which it is communicatively coupled. A further hardware-implemented module/component may then, at a later time, access the memory device to retrieve and process the stored output. Hardware-implemented modules/components may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules/components that operate to perform one or more operations or functions. The modules/components referred to herein may, in some examples, comprise processor-implemented modules/components.

Similarly, the methods described herein may be at least partially processor-implemented. For example, at least some of the operations of a method may be performed by one or more processors or processor-implemented modules/components. The performance of certain of the operations may be distributed among the one or more processors, not only residing within a single machine, but deployed across a number of machines. In some examples, the processor or processors may be located in a single location (e.g., within a home environment, an office environment, or a server farm), while in other examples the processors may be distributed across a number of locations.

The one or more processors may also operate to support performance of the relevant operations in a "cloud computing" environment or as a "software as a service (SaaS)." For example, at least some of the operations may be performed by a group of computers (as examples of machines including processors), these operations being accessible via a network (e.g., the Internet) and via one or more appropriate interfaces (e.g., APIs).

Examples may be implemented in digital electronic circuitry, or in computer hardware, firmware, or software, or in combinations of them. Examples may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a standalone program or as a module, subroutine, or other unit suitable for use in a computing environment. A computer program can be deployed to be executed on one computer or on multiple computers at one site or distributed across multiple sites and interconnected by a communication network.

In examples, operations may be performed by one or more programmable processors executing a computer program to perform functions by operating on input data and generating output. Method operations can also be performed by, and apparatus of some examples may be implemented as, special purpose logic circuitry, e.g., an FPGA or an ASIC.

The computing system can include clients and servers. A client and server are generally remote from each other and typically interact through a communication network. The relationship of client and server arises by virtue of computer programs running on the respective computers and having a client-server relationship to each other. In examples deploying a programmable computing system, it will be appreciated that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or in a combination of permanently and temporarily configured hardware may be a design choice. Below are set out hardware (e.g., machine) and software architectures that may be deployed, in various examples.

Figure 7:
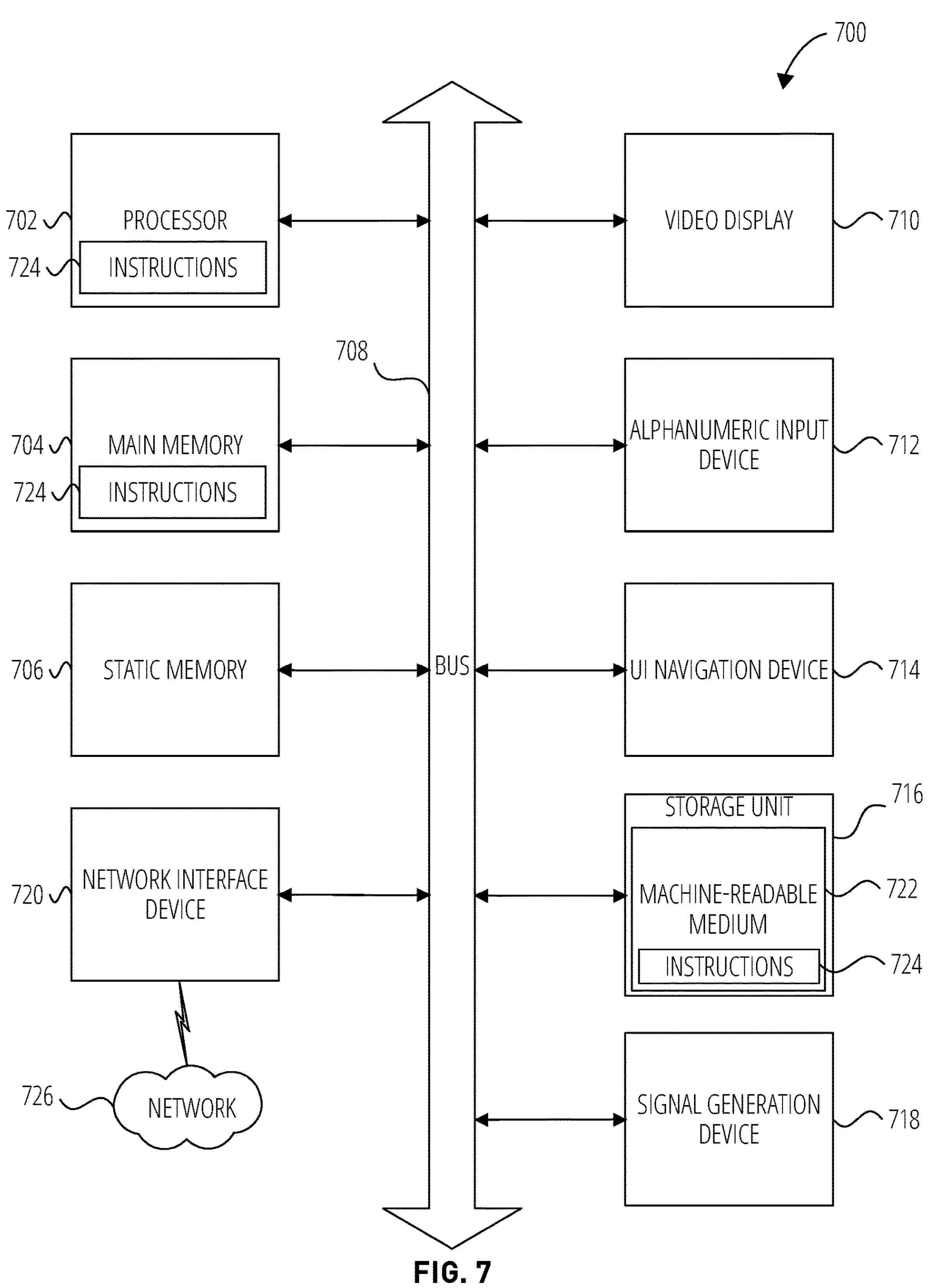
FIG. 7 is a block diagram of a machine in the form of a computer system, according to some examples, within which instructions may be executed for causing the machine to perform any one or more of the methodologies discussed herein.

FIG. 7 is a block diagram of a machine in the example form of a computer system 700 within which instructions 724 may be executed for causing the machine to perform any one or more of the methodologies discussed herein. In alternative examples, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a personal digital assistant (PDA), a cellular telephone, a web appliance, a network router, switch, or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 700 includes a processor 702, a primary or main memory 704, and a static memory 706, which communicate with each other via a bus 708. The computer system 700 may further include a video display unit 710 (e.g., a liquid crystal display (LCD) or a cathode ray tube (CRT)). The computer system 700 may also include an alphanumeric input device 712 (e.g., a keyboard or a touch-sensitive display screen), a UI navigation (or cursor control) device 714 (e.g., a mouse), a storage unit 716, a signal generation device 718 (e.g., a speaker), and a network interface device 720.

As used herein, the term "processor" may refer to any one or more circuits or virtual circuits (e.g., a physical circuit emulated by logic executing on an actual processor) that manipulates data values according to control signals (e.g., commands, opcodes, machine code, control words, macroinstructions, etc.) and which produces corresponding output signals that are applied to operate a machine. A processor may, for example, include at least one of a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), a Tensor Processing Unit (TPU), a Neural Processing Unit (NPU), a Vision Processing Unit (VPU), a Machine Learning Accelerator, an Artificial Intelligence Accelerator, an Application Specific Integrated Circuit (ASIC), an FPGA, a Radio-Frequency Integrated Circuit (RFIC), a Neuromorphic Processor, a Quantum Processor, or any combination thereof. A processor may be a multi-core processor having two or more independent processors (sometimes referred to as "cores") that may execute instructions contemporaneously. Multi-core processors may contain multiple computational cores on a single integrated circuit die, each of which can independently execute program instructions in parallel. Parallel processing on multi-core processors may be implemented via architectures like superscalar, VLIW, vector processing, or SIMD that allow each core to run separate instruction streams concurrently. A processor may be emulated in software, running on a physical processor, as a virtual processor or virtual circuit. The virtual processor may behave like an independent processor but is implemented in software rather than hardware.

The storage unit 716 includes a machine-readable medium 722 on which is stored one or more sets of data structures and instructions 724 (e.g., software) embodying or utilized by any one or more of the methodologies or functions described herein. The instructions 724 may also reside, completely or at least partially, within the main memory 704 or within the processor 702 during execution thereof by the computer system 700, with the main memory 704 and the processor 702 also each constituting a machine-readable medium 722.

While the machine-readable medium 722 is shown in accordance with some examples to be a single medium, the term "machine-readable medium" may include a single medium or multiple media (e.g., a centralized or distributed database, or associated caches and servers) that store the one or more instructions 724 or data structures. The term "machine-readable medium" shall also be taken to include any tangible medium that is capable of storing, encoding, or carrying instructions 724 for execution by the machine and that cause the machine to perform any one or more of the methodologies of the present disclosure, or that is capable of storing, encoding, or carrying data structures utilized by or associated with such instructions 724. The term "machine-readable medium" shall accordingly be taken to include, but not be limited to, solid-state memories, and optical and magnetic media. Specific examples of a machine-readable medium 722 include non-volatile memory, including by way of example semiconductor memory devices, e.g., erasable programmable read-only memory (EPROM), electrically erasable programmable read-only memory (EEPROM), and flash memory devices; magnetic disks such as internal hard disks and removable disks; magneto-optical disks; and compact disc read-only memory (CD-ROM) and digital versatile disc read-only memory (DVD-ROM) disks. A machine-readable medium is not a transmission medium.

The instructions 724 may further be transmitted or received over a communications network 726 using a transmission medium. The instructions 724 may be transmitted using the network interface device 720 and any one of a number of well-known transfer protocols (e.g., hypertext transport protocol (HTTP)). Examples of communication networks include a local area network (LAN), a wide area network (WAN), the Internet, mobile telephone networks, plain old telephone (POTS) networks, and wireless data networks. The term "transmission medium" shall be taken to include any intangible medium that is capable of storing, encoding, or carrying instructions 724 for execution by the machine, and includes digital or analog communications signals or other intangible media to facilitate communication of such software.

Although specific examples are described herein, it will be evident that various modifications and changes may be made to these examples without departing from the broader spirit and scope of the disclosure. Accordingly, the specification and drawings are to be regarded in an illustrative rather than a restrictive sense. The accompanying drawings that form a part hereof show by way of illustration, and not of limitation, specific examples in which the subject matter may be practiced. The examples illustrated are described in sufficient detail to enable those skilled in the art to practice the teachings disclosed herein. Other examples may be utilized and derived therefrom, such that structural and logical substitutions and changes may be made without departing from the scope of this disclosure. This detailed description, therefore, is not to be taken in a limiting sense, and the scope of various examples is defined only by the appended claims, along with the full range of equivalents to which such claims are entitled.

Such examples of the inventive subject matter may be referred to herein, individually or collectively, by the "example" merely for convenience and without intending to voluntarily limit the scope of this application to any single example or concept if more than one is in fact disclosed. Thus, although specific examples have been illustrated and described herein, it should be appreciated that any arrangement calculated to achieve the same purpose may be substituted for the specific examples shown. This disclosure is intended to cover any and all adaptations or variations of various examples. Combinations of the above examples, and other examples not specifically described herein, will be apparent to those of skill in the art upon reviewing the above description.

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" and "an" are herein used, as is common in patent documents, to include one or more than one instance.

Unless the context clearly requires otherwise, throughout the description and the claims, the words "comprise," "comprising," and the like are to be construed in an inclusive sense, as opposed to an exclusive or exhaustive sense, e.g., in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words using the singular or plural number may also include the plural or singular number, respectively. The word "or" in reference to a list of two or more items, covers all of the following interpretations of the word: any one of the items in the list, all of the items in the list, and any combination of the items in the list.

Although some examples, such as those depicted in the drawings, may include a particular sequence of operations, the sequence may be altered without departing from the scope of the present disclosure. For example, some of the operations depicted may be performed in parallel or in a different sequence that does not materially affect the functions as described in the examples. In other examples, different components of an example device or system that implements an example method may perform functions at substantially the same time or in a specific sequence. The term "operation" may be used to refer to elements in the drawings of this disclosure for ease of reference and it will be appreciated that each "operation" may identify one or more operations, processes, actions, or steps, and may be performed by one or multiple components.

From a machine learning perspective, examples of specific machine learning algorithms are provided in examples herein. However, it is noted that various machine learning algorithms may be deployed, according to some examples, and depending on the use case. For example, logistic regression, which is a type of supervised learning algorithm, can be used for binary classification tasks. Logistic regression models the probability of a binary response variable based on one or more predictor variables. Another example type of machine learning algorithm is Naïve Bayes, which is a supervised learning algorithm used for classification tasks. Naïve Bayes is based on Bayes' theorem and assumes that the predictor variables are independent of each other. Random forest is another type of supervised learning algorithm used for classification, regression, and other tasks. Random forest builds a collection of decision trees and combines their outputs to make predictions. Further examples include neural networks, which consist of interconnected layers of nodes (or neurons) that process information and make predictions based on the input data. Matrix factorization is another type of machine learning algorithm used for recommender systems and other tasks. Matrix factorization decomposes a matrix into two or more matrices to uncover hidden patterns or relationships in the data. Support Vector Machines (SVM) are a type of supervised learning algorithm used for classification, regression, and other tasks. SVM finds a hyperplane that separates the different classes in the data. Other types of machine learning algorithms may include decision trees, k-nearest neighbors, clustering algorithms, and deep learning algorithms, such as Convolutional Neural Networks (CNN), Recurrent Neural Networks (RNN), and transformer models. The choice of algorithm may depend on, for example, the nature of the data, the complexity of the problem, and the performance requirements of the application. Deep learning algorithms such as convolutional neural networks, recurrent neural networks, and transformers, as well as more traditional machine learning algorithms like decision trees, random forests, and gradient boosting may be used in various machine learning applications.

The performance of a machine learning model may be evaluated on a separate test set of data that was not used during training to ensure that the model can generalize to new, unseen data. In addition to a training phase, a validation phase may be performed on a separate dataset known as the validation dataset. The validation dataset is used to tune the hyperparameters of a model, such as the learning rate and the regularization parameter. The hyperparameters are adjusted to improve the model's performance on the validation dataset.

In a prediction or inference phase, the trained machine learning model uses the relevant features for analyzing query data to generate inferences, outcomes, or predictions. In some examples, a machine learning model may be fine-tuned, e.g., after initial deployment. The term "fine-tuning," as used herein, generally refers to a process of adapting a pre-trained machine learning model. For example, a machine learning model may be adapted to improve its performance on a specific task or to make it more suitable for a specific operation. Fine-tuning techniques may include one or more of updating or changing a pre-trained model's internal parameters through additional training, injecting new trainable weights or layers into the model architecture and training on those weights or layers, modifying a model topology by altering layers or connections, changing aspects of the training process (such as loss functions or optimization methods), or any other adaptations that may, for example, result in better model performance on a particular task compared to the pre-trained model.

As used in this disclosure, the term "machine learning model" (or simply "model") may refer to a single, standalone model, or a combination of models. The term may also refer to a system, component or module that includes a machine learning model together with one or more supporting or supplementary components that do not necessarily perform machine learning tasks.

In view of the above-described implementations of subject matter this application discloses the following list of examples, wherein one feature of an example in isolation or more than one feature of an example, taken in combination and, optionally, in combination with one or more features of one or more further examples are further examples also falling within the disclosure of this application.

Example 1 is a system comprising: at least one memory that stores instructions; and one or more processors configured by the instructions to perform operations comprising: accessing first data indicative of a baseline condition of a first user associated with a digital physical therapy program; collecting, for each of a plurality of sessions of the digital physical therapy program, second data indicative of at least one condition status of the first user, wherein a first device associated with the first user tracks motion of the first user via one or more sensors during each of the plurality of sessions to automatically obtain at least some of the second data; providing input data to a machine learning classifier to cause generation of output data indicative of a predicted outcome of the digital physical therapy program, the input data being based on the first data and the second data; detecting, based on the predicted outcome, that the first user is predicted not to meet a predetermined improvement threshold; and in response to detecting that the first user is predicted not to meet the predetermined improvement threshold: automatically generating an alert associated with the first user, and causing presentation of the alert at a second device associated with a second user administering at least part of the digital physical therapy program.

In Example 2, the subject matter of Example 1 includes, the operations further comprising: preprocessing the second data from the plurality of sessions by applying at least one longitudinal evolution model to obtain preprocessed second data, wherein the input data provided to the machine learning classifier includes the preprocessed second data.

In Example 3, the subject matter of Example 2 includes, the operations further comprising: generating, using a training data set, the at least one longitudinal evolution model; and applying the at least one longitudinal evolution model to train the machine learning classifier on at least a subset of the training data set.

In Example 4, the subject matter of any of Examples 2-3 includes, wherein the at least one longitudinal evolution model comprises at least one of: a longitudinal evolution model that provides clusters of trajectories for pain, a longitudinal evolution model that provides clusters of trajectories for fatigue, or a longitudinal evolution model indicative of latent range of motion.

In Example 5, the subject matter of any of Examples 1~4 includes, the operations further comprising: identifying a feature associated with the input data as a driver of the predicted outcome, wherein the alert presented at the second device comprises an indication of the driver.

In Example 6, the subject matter of Example 5 includes, wherein the feature is identified as the driver based on one or more prediction-explaining values.

In Example 7, the subject matter of any of Examples 1-6 includes, wherein the first data comprises at least one of a baseline pain level of the first user, demographic data of the first user, clinical data of the first user, prescription data of the first user, behavioral data of the first user, or social data of the first user, and wherein the second data comprises at least one of range of motion data automatically collected via the one or more sensors, a pain level of the first user after a session, a fatigue level of the first user after a session, or utilization data associated with the digital physical therapy program.

In Example 8, the subject matter of Example 7 includes, wherein the second data comprises, for each session, automatically collected data and user-reported data.

In Example 9, the subject matter of any of Examples 1-8 includes, wherein the plurality of sessions is a predetermined number of sessions, and the predicted outcome is automatically generated by the machine learning classifier upon conclusion of the predetermined number of sessions and prior to conclusion of the digital physical therapy program.

In Example 10, the subject matter of Example 9 includes, wherein the predetermined number of sessions is between two and twelve sessions.

In Example 11, the subject matter of any of Examples 1-10 includes, wherein the machine learning classifier comprises a tree-based ensemble classifier model trained using supervised learning.

In Example 12, the subject matter of Example 11 includes, wherein the tree-based ensemble classifier model comprises at least one of a random forest or a gradient-boosting decision tree.

In Example 13, the subject matter of any of Examples 1-12 includes, wherein the second user is a physical therapist assigned to the first user, the operations further comprising: generating a therapy workflow comprising one or more actions for the digital physical therapy program associated with the first user; storing, in a database, the therapy workflow in association with the second user; adjusting the therapy workflow based on the predicted outcome; and causing presentation of the adjusted therapy workflow at the second device.

In Example 14, the subject matter of Example 13 includes, wherein the adjustment of the therapy workflow comprises: assigning a priority indicator to the first user; and causing presentation of the priority indicator at the second device, the priority indicator being presented in a user interface that includes at least part of the therapy workflow.

In Example 15, the subject matter of any of Examples 1-14 includes, wherein the output data generated by the machine learning classifier comprises a likelihood score, the operations further comprising: collecting, subsequent to the plurality of sessions, third data for an additional session of the digital physical therapy program, at least some of the third data being automatically obtained via the one or more sensors; generating, using the machine learning classifier and based at least on the third data, updated output data comprising an updated likelihood score; and applying the updated likelihood score to determine whether the predicted outcome has changed.

In Example 16, the subject matter of any of Examples 1-15 includes, wherein the digital physical therapy program comprises a plurality of exercises designed to treat a musculoskeletal (MSK) condition in the first user, the one or more sensors tracking the motion of the first user while the first user performs each of the plurality of exercises.

In Example 17, the subject matter of any of Examples 1-16 includes, wherein the predetermined improvement threshold is associated with a pain level of the first user, and the predetermined improvement threshold comprises at least one of: the pain level of the first user is at or below a predetermined pain threshold upon conclusion of the digital physical therapy program, or the first user has a predetermined reduction in the pain level upon conclusion of the digital physical therapy program.

In Example 18, the subject matter of any of Examples 1-17 includes, wherein the first device is a computing device that includes or is communicatively coupled to the one or more sensors, the one or more sensors comprising at least one of a camera or a motion tracker.

Example 19 is a method comprising: accessing, by one or more computing devices, first data indicative of a baseline condition of a first user associated with a digital physical therapy program; collecting, by the one or more computing devices and for each of a plurality of sessions of the digital physical therapy program, second data indicative of at least one condition status of the first user, wherein a first device associated with the first user tracks motion of the first user via one or more sensors during each of the plurality of sessions to automatically obtain at least some of the second data; providing, by the one or more computing devices, input data to a machine learning classifier to cause generation of output data indicative of a predicted outcome of the digital physical therapy program, the input data being based on the first data and the second data; detecting, by the one or more computing devices and based on the predicted outcome, that the first user is predicted not to meet a predetermined improvement threshold; and in response to detecting that the first user is predicted not to meet the predetermined improvement threshold: automatically generating, by the one or more computing devices, an alert associated with the first user, and causing, by the one or more computing devices, presentation of the alert at a second device associated with a second user administering at least part of the digital physical therapy program.

Example 20 is a non-transitory computer-readable medium that stores instructions that, when executed by one or more processors, cause the one or more processors to perform operations comprising: accessing first data indicative of a baseline condition of a first user associated with a digital physical therapy program; collecting, for each of a plurality of sessions of the digital physical therapy program, second data indicative of at least one condition status of the first user, wherein a first device associated with the first user tracks motion of the first user via one or more sensors during each of the plurality of sessions to automatically obtain at least some of the second data; providing input data to a machine learning classifier to cause generation of output data indicative of a predicted outcome of the digital physical therapy program, the input data being based on the first data and the second data; detecting, based on the predicted outcome, that the first user is predicted not to meet a predetermined improvement threshold; and in response to detecting that the first user is predicted not to meet the predetermined improvement threshold: automatically generating an alert associated with the first user, and causing presentation of the alert at a second device associated with a second user administering at least part of the digital physical therapy program.

Example 21 is at least one machine-readable medium including instructions that, when executed by processing circuitry, cause the processing circuitry to perform operations to implement any of Examples 1-20.

Example 22 is an apparatus comprising means to implement any of Examples 1-20.

Example 23 is a system to implement any of Examples 1-20.

Example 24 is a method to implement any of Examples 1-20.

What is claimed is:

1. A system comprising:

at least one memory that stores instructions; and one or more processors configured by the instructions to perform operations comprising:

accessing first data indicative of a baseline condition of a first user associated with a digital physical therapy program;

collecting, for at least a subset of a set of sessions of the digital physical therapy program, second data indicative of at least one condition status of the first user, wherein a first device associated with the first user tracks motion of the first user via one or more sensors during each of the subset of sessions to automatically obtain at least some of the second data;

predicting, based on the first data and the second data, trajectory data characterizing changes in a patient health metric of the first user through the digital physical therapy program;

providing input data to a machine learning classifier to cause generation of output data indicative of a predicted outcome of the digital physical therapy program based on an evaluation of the trajectory data relative to a timeline of the set of sessions of the digital physical therapy program, the input data being based on the first data, the second data, and the trajectory data;

detecting, based on the predicted outcome, that the first user is predicted not to meet a predetermined improvement threshold, the predetermined improvement threshold defining a target level of change for the patient health metric of the first user between a beginning and an end of the set of sessions of the digital physical therapy program; and in response to detecting that the first user is predicted not to meet the predetermined improvement threshold:

automatically generating an alert associated with the first user, causing presentation of the alert at a second device associated with a second user administering at least part of the digital physical therapy program, automatically adjusting an exercise duration of at least one session of a remaining subset of the set of sessions in the digital physical therapy program to generate an adjusted digital physical therapy program, and monitoring the remaining subset of the set of sessions with the first device to measure performance of the adjusted digital physical therapy program.

2. The system of claim 1, the operations further comprising:

preprocessing the second data from the subset of sessions by applying at least one longitudinal evolution model to obtain preprocessed second data, wherein the input data provided to the machine learning classifier includes the preprocessed second data.

3. The system of claim 2, the operations further comprising:

generating, using a training data set, the at least one longitudinal evolution model; and applying the at least one longitudinal evolution model to train the machine learning classifier on at least a subset of the training data set.

4. The system of claim 2, wherein the at least one longitudinal evolution model comprises at least one of: a longitudinal evolution model that provides clusters of trajectories for pain, a longitudinal evolution model that provides clusters of trajectories for fatigue, or a longitudinal evolution model indicative of latent range of motion.

5. The system of claim 1, the operations further comprising:

identifying a feature associated with the input data as a driver of the predicted outcome, wherein the alert presented at the second device comprises an indication of the driver.

6. The system of claim 5, wherein the feature is identified as the driver based on one or more prediction-explaining values.

7. The system of claim 1, wherein the first data comprises at least one of a baseline pain level of the first user, demographic data of the first user, clinical data of the first user, prescription data of the first user, behavioral data of the first user, or social data of the first user, and wherein the second data comprises at least one of range of motion data automatically collected via the one or more sensors, a pain level of the first user after a session, a fatigue level of the first user after a session, or utilization data associated with the digital physical therapy program.

8. The system of claim 7, wherein the second data comprises, for each session, automatically collected data and user-reported data.

9. The system of claim 1, wherein the subset of sessions is a predetermined number of sessions, and the predicted outcome is automatically generated by the machine learning classifier upon conclusion of the predetermined number of sessions and prior to conclusion of the digital physical therapy program.

10. The system of claim 9, wherein the predetermined number of sessions is between two and twelve sessions, and monitoring the remaining subset of the set of sessions comprises:

adjusting an exercise schedule or the exercise duration in the adjusted digital physical therapy program to generate a second adjusted digital physical therapy program based on a second predicted outcome that the first user is predicted not to meet the predetermined improvement threshold.

11. The system of claim 1, wherein the machine learning classifier comprises a tree-based ensemble classifier model trained using supervised learning.

12. The system of claim 11, wherein the tree-based ensemble classifier model comprises at least one of a random forest or a gradient-boosting decision tree.

13. The system of claim 1, wherein the second user is a physical therapist assigned to the first user, the operations further comprising:

generating a therapy workflow comprising one or more actions for the digital physical therapy program associated with the first user, storing, in a database, the therapy workflow in association with the second user;

adjusting the therapy workflow based on the predicted outcome; and causing presentation of the adjusted therapy workflow at the second device.

14. The system of claim 13, wherein the adjustment of the therapy workflow comprises:

assigning a priority indicator to the first user; and causing presentation of the priority indicator at the second device, the priority indicator being presented in a user interface that includes at least part of the therapy workflow.

15. The system of claim 1, wherein the output data generated by the machine learning classifier comprises a likelihood score, the operations further comprising:

collecting, subsequent to the subset of sessions, third data for an additional session of the digital physical therapy program, at least some of the third data being automatically obtained via the one or more sensors;

generating, using the machine learning classifier and based at least on the third data, updated output data comprising an updated likelihood score; and applying the updated likelihood score to determine whether the predicted outcome has changed.

16. The system of claim 1, wherein the digital physical therapy program comprises a plurality of exercises designed to treat a musculoskeletal (MSK) condition in the first user, the one or more sensors tracking the motion of the first user while the first user performs each of the plurality of exercises.

17. The system of claim 1, wherein the predetermined improvement threshold is associated with a pain level of the first user, and the predetermined improvement threshold comprises at least one of: the pain level of the first user is at or below a predetermined pain threshold upon conclusion of the digital physical therapy program, or the first user has a predetermined reduction in the pain level upon conclusion of the digital physical therapy program.

18. The system of claim 1, wherein the first device is a computing device that includes or is communicatively coupled to the one or more sensors, the one or more sensors comprising at least one of a camera or a motion tracker.

19. A method comprising:

accessing, by one or more computing devices, first data indicative of a baseline condition of a first user associated with a digital physical therapy program;

collecting, by the one or more computing devices and for at least a subset of a set of sessions of the digital physical therapy program, second data indicative of at least one condition status of the first user, wherein a first device associated with the first user tracks motion of the first user via one or more sensors during each of the subset of sessions to automatically obtain at least some of the second data;

predicting, by the one or more computing devices, based on the first data and the second data, trajectory data characterizing changes in a patient health metric of the first user through the digital physical therapy program;

providing, by the one or more computing devices, input data to a machine learning classifier to cause generation of output data indicative of a predicted outcome of the digital physical therapy program based on an evaluation of the trajectory data relative to a timeline of the set of sessions of the digital physical therapy program, the input data being based on the first data, the second data, and the trajectory data;

detecting, by the one or more computing devices and based on the predicted outcome, that the first user is predicted not to meet a predetermined improvement threshold, the predetermined improvement threshold defining a target level of change for a patient health metric of the first user between a beginning and an end of the set of sessions of the digital physical therapy program; and in response to detecting that the first user is predicted not to meet the predetermined improvement threshold:

automatically generating, by the one or more computing devices, an alert associated with the first user, causing, by the one or more computing devices, presentation of the alert at a second device associated with a second user administering at least part of the digital physical therapy program, automatically adjusting, by the one or more computing devices, an exercise duration of at least one session of a remaining subset of the set of sessions in the digital physical therapy program to generate an adjusted digital physical therapy program, and monitoring, by the one or more computing devices, the remaining subset of the set of sessions with the first device to measure performance of the adjusted digital physical therapy program.

20. A non-transitory computer-readable medium that stores instructions that, when executed by one or more processors, cause the one or more processors to perform operations comprising:

accessing first data indicative of a baseline condition of a first user associated with a digital physical therapy program;

collecting, for at least a subset of a set of sessions of the digital physical therapy program, second data indicative of at least one condition status of the first user, wherein a first device associated with the first user tracks motion of the first user via one or more sensors during each of the subset of sessions to automatically obtain at least some of the second data;

predicting, based on the first data and the second data, trajectory data characterizing changes in a patient health metric of the first user through the digital physical therapy program;

providing input data to a machine learning classifier to cause generation of output data indicative of a predicted outcome of the digital physical therapy program based on an evaluation of the trajectory data relative to a timeline of the set of sessions of the digital physical therapy program, the input data being based on the first data, the second data, and the trajectory data;

detecting, based on the predicted outcome, that the first user is predicted not to meet a predetermined improvement threshold, the predetermined improvement threshold defining a target level of change for a patient health metric of the first user between a beginning and an end of the set of sessions of the digital physical therapy program, and in response to detecting that the first user is predicted not to meet the predetermined improvement threshold:

automatically generating an alert associated with the first user, causing presentation of the alert at a second device associated with a second user administering at least part of the digital physical therapy program, automatically adjusting an exercise duration of at least one session of a remaining subset of the set of sessions in the digital physical therapy program to generate an adjusted digital physical therapy program, and monitoring the remaining subset of the set of sessions with the first device to measure performance of the adjusted digital physical therapy program.

* * * * *